(12) United States Patent
Castel et al.

(10) Patent No.: US 8,473,064 B2
(45) Date of Patent: Jun. 25, 2013

(54) ELECTRICAL STIMULATION METHOD FOR REDUCTION OF JOINT COMPRESSION

(75) Inventors: J. Chris Castel, Reno, NV (US); Frank Palermo, Lafayette, CO (US)

(73) Assignee: Accelerated Care Plus Corp., Reno, NV (US)

( * ) Notice: Subject to any disclaimer, the term of this patent is extended or adjusted under 35 U.S.C. 154(b) by 754 days.

(21) Appl. No.: 12/487,431

(22) Filed: Jun. 18, 2009

(65) Prior Publication Data
US 2009/0319003 A1  Dec. 24, 2009

Related U.S. Application Data

(60) Provisional application No. 61/073,653, filed on Jun. 18, 2008.

(51) Int. Cl.
*A61N 1/04* (2006.01)
(52) U.S. Cl.
USPC ............................................. 607/48; 607/49
(58) Field of Classification Search
USPC ........................ 607/46, 48, 49, 148
See application file for complete search history.

(56) References Cited

U.S. PATENT DOCUMENTS

| | | | |
|---|---|---|---|
| 5,562,718 A | 10/1996 | Palermo | |
| 6,185,455 B1 * | 2/2001 | Loeb et al. | 607/3 |
| 6,393,328 B1 | 5/2002 | McGraw et al. | |
| 7,232,415 B2 | 6/2007 | Steinberg | |
| 2002/0143373 A1 | 10/2002 | Courtnage | |
| 2004/0054379 A1 | 3/2004 | Carroll et al. | |
| 2004/0220645 A1 * | 11/2004 | Freed et al. | 607/48 |
| 2006/0079800 A1 | 4/2006 | Martikka | |
| 2007/0038252 A1 | 2/2007 | Carroll | |

FOREIGN PATENT DOCUMENTS

WO   WO 2007/063383   6/2007

* cited by examiner

*Primary Examiner* — Tammie K Heller
(74) *Attorney, Agent, or Firm* — Stinson Morrison Hecker LLP

(57) ABSTRACT

An electrical stimulation method for the reduction of joint compression utilizes an electrical stimulation device that includes a plurality of channels of electrodes each of which includes at least a first and second electrode positioned in electrical contact with tissue of at least two muscles crossing a joint. Agonist/antagonist muscles involved in abduction/adduction, flexion/extension, supination/pronation, protraction/retraction, and/or eversion/inversion of body regions via joint movement are stimulated with a patterned series of electrical pulses through channels of electrodes in accordance with a procedure for reducing joint compression. The patterned series of electrical pulses may comprise: a plurality of cycles of a biphasic sequential pulse train pattern; a plurality of cycles of a biphasic overlapping pulse train pattern; a plurality of cycles of a triphasic sequential pulse train pattern; and a plurality of cycles of a triphasic overlapping pulse train pattern.

29 Claims, 19 Drawing Sheets

VAS Score (Pain)

ELECTRICAL STIMULATION METHOD FOR REDUCTION OF JOINT COMPRESSION

CROSS-REFERENCE TO RELATED APPLICATIONS

Not applicable.

STATEMENT REGARDING FEDERALLY SPONSORED RESEARCH OR DEVELOPMENT

Not applicable.

FIELD OF THE INVENTION

The present invention is generally directed to a method for reducing joint compression, and is more specifically directed to an electrical stimulation method for applying a patterned series of electrical pulses to a plurality of channels of electrodes in accordance with a procedure for reducing joint compression. The method results in improved muscle and nerve timing, which reduces co-activation of muscles associated with joints during movement or during stabilization.

DESCRIPTION OF RELATED ART

The junction of two or more bones or skeletal parts is a joint. There are several types of human joints including fibrous (non-movable), cartilaginous (connected entirely by cartilage), and synovial joints. A synovial joint is a freely movable articulation, in which contiguous bone surfaces are covered with collagenous fibrovascular tissue composed of flattened or cuboidal cells. The collagenous fibrovascular tissue is called articular cartilage. Examples of human synovial joints include the elbow, shoulder, wrist, ankle, knee, hip, and intervertebral joints.

In a healthy human synovial joint, a synovial membrane surrounds the articular cartilage and contains synovial fluid. Synovial fluid is normally clear, resembling egg white. Synovial fluid lubricates the joint by providing a thin liquid layer over the articular cartilage. The synovial fluid also carries oxygen and nutrients to the articular cartilage by diffusing into the spaces in the articular cartilage during non-movement. During movement, the synovial fluid is squeezed out of the articular cartilage to maintain the surface liquid layer for lubrication and carry waste away from the articular cartilage. When the joint is at rest again, the synovial fluid diffuses back into the articular cartilage carrying with it a supply of nutrients and oxygen that it obtained from the increased blood flow around the joint during movement. The health of the articular cartilage is dependent upon the extrusion and diffusion of the synovial fluid normally caused by joint movement.

A common form of joint pain and/or stiffness arises from the unwanted co-contraction of muscles. The simultaneous contraction of an antagonist muscle and its corresponding agonist muscle is termed "co-contraction". The co-contraction causes joint compression, which results in the degeneration or "wear and tear" of articular cartilage and is usually accompanied by an overgrowth of bone, narrowing of the joint space, sclerosis or hardening of bone at the joint surface, and deformity in joints. Weight bearing joints, such as the knees and hips, are particularly susceptible to osteoarthritis.

Unwanted involuntary muscle co-contraction, as a response to an abnormal stimulus such as pain during joint movement, can be destructive to the joint over time. Sustained co-contraction increases the local level of norepinephrine. Norepinephrine causes vasoconstriction, which decreases blood flow. Decreased blood flow prevents the synovial fluid from picking up oxygen and nutrients to carry back to the articular cartilage. In addition to decreasing blood flow, sustained co-contraction of opposing muscle groups has a net effect of increasing the compressive force across the joint. The constant increased compressive force squeezes the synovial fluid out of the articular cartilage and prevents it from diffusing back in thereby starving the articular cartilage of oxygen and nutrients. The starved articular cartilage deteriorates, which leads to additional pain, decreased coordination, increased joint stiffness, and eventual total joint degeneration.

Carroll et al., U.S. Patent Application 2004/0054379 teaches the use of surface electrical simulation for increasing the quality and quantity of synovial fluid in joints. The patent emphasizes that the electrical simulation is that which "mimics normal electrical sequencing of surrounding muscles of the joint during normal functioning activity." See Para 0016. Thus, Carroll utilizes a functional sequence which causes the joint to move.

BRIEF SUMMARY OF THE INVENTION

The present invention is directed to an electrical stimulation method for reducing joint compression in a patient by decreasing the unwanted co-contraction of agonist/antagonist muscle pairs associated with a joint. In general, the electrical stimulation method utilizes an electronic control unit connected to two or more channels of electrodes, such as transcutaneous or percutaneous electrodes. Each channel comprises at least two electrodes (i.e., at least one relative positive electrode and at least one relative negative electrode), wherein one electrode is positioned in electrical contact with a first tissue of a first muscle of a target joint of a patient and the other electrode is positioned in electrical contact with a second tissue of a second muscle of a target joint of a patient. The electrical control unit applies a series of electrical pulses having a biphasic or triphasic pattern to the patient through the two or more channels of electrodes in accordance with a procedure for reducing joint compression in the patient.

In one aspect, the electrical stimulation method stimulates the sensory and motor nerves of the patient's musculature associated with opposing joint movement. For example, electrodes can be positioned bilaterally or in electrical contact with the tissue of agonist/antagonist muscle pairs in the neck, trunk, shoulder, arm, wrist, hand, hip, thigh, lower leg, ankle, and foot of the patient that are associated with a joint. Examples of agonist/antagonist muscle pairs include abductors/adductors, flexors/extensors, supinators/pronators, protractors/retractors, and evertors/inverters. For example, both the flexor carpi radialis and flexor carpi ulnaris are flexors of the wrist. The extensor carpi radialis longus, in conjunction with extensor carpi radialis brevis, is an extensor of the wrist.

In a first embodiment, the electrical stimulation method can be used to stimulate the muscles associated with the cervical intervertebral joints. For example, the electrodes are positioned in electrical contact with tissue to stimulate a motor point of a patient's trapezius muscle and cervical paraspinal muscles.

In a second embodiment, the electrical stimulation method can be used to stimulate the muscles associated with the lower cervical and upper thoracic intervertebral joints. For example, the electrodes are positioned in electrical contact with tissue to stimulate a motor point of a patient's trapezius muscle and cervical and/or thoracic paraspinal muscles.

In a third embodiment, the electrical stimulation method can be used to stimulate the muscles associated with the upper thoracic intervertebral joints. For example, the electrodes are positioned in electrical contact with tissue to stimulate a motor point of a patient's trapezius muscle, erector spinae muscle, and thoracic paraspinal muscles.

In a fourth embodiment, the electrical stimulation method can be used to stimulate the muscles associated with the lower thoracic and lumbar intervertebral joints. For example, the electrodes are positioned in electrical contact with tissue to stimulate a motor point of a patient's lower thoracic and lumbar paraspinal muscles and abdominal muscles.

In a fifth embodiment, the electrical stimulation method can be used to stimulate the muscles associated with the lower thoracic and lumbar intervertebral joints. For example, the electrodes are positioned in electrical contact with tissue to stimulate a motor point of a patient's multifidus muscle and abdominal muscles.

In a sixth embodiment, the electrical stimulation method can be used to stimulate the muscles associated with the elbow joint. For example, the electrodes are positioned in electrical contact with tissue to stimulate a motor point of a patient's biceps brachii muscle and triceps brachii muscle.

In a seventh embodiment, the electrical stimulation method can be used to stimulate the muscles associated with the shoulder joint. For example, the electrodes are positioned in electrical contact with tissue to stimulate a motor point of a patient's biceps brachii, pectoralis major, anterior deltoid, triceps brachii, infraspinatus teres minor, and posterior deltoid muscles.

In an eighth embodiment, the electrical stimulation method can be used to stimulate the muscles associated with the shoulder and elbow joints. For example, the electrodes are positioned in electrical contact with tissue to stimulate a motor point of a patient's biceps brachii muscle, anterior deltoid muscle, triceps brachii muscle, and posterior deltoid muscle.

In a ninth embodiment, the electrical stimulation method can be used to stimulate the muscles associated with the wrist joint. For example, the electrodes are positioned in electrical contact with tissue to stimulate a motor point of a patient's flexor digitorum superficialis muscle, flexor carpi radialis muscle, flexor carpi ulnaris muscle, extensor digitorum muscle, pollicis muscle, extensor digiti minimi muscle, extensor carpi ulnaris muscle, extensor carpi radialis longus muscle, and/or carpi radialis brevis muscle.

In a tenth embodiment, the electrical stimulation method can be used to stimulate the muscles associated with the wrist and elbow joints. For example, the electrodes are positioned in electrical contact with tissue to stimulate a motor point of a patient's biceps brachii muscle, triceps brachii muscle, intrinsic hand muscles, and/or extensor muscles of the forearm.

In an eleventh embodiment, the electrical stimulation method can be used to stimulate the muscles associated with the ankle joint. For example, the electrodes are positioned in electrical contact with tissue to stimulate a motor point of a patient's extensor digitorum brevis muscle, tibialis anterior muscle, extensor digitorum longus muscle, extensor hallucis longus muscle, posterior tibialis muscle, flexor hallucis muscle, and/or intrinsic foot muscles including abductor hallucis muscle.

In a twelfth embodiment, the electrical stimulation method can be used to stimulate the muscles associated with the ankle joint. For example, the electrodes are positioned in electrical contact with tissue to stimulate a motor point of a patient's tibialis anterior muscle, triceps surae muscle group including gastrocnemius and soleus muscles, and/or anterior and lateral muscles of the leg including the peroneus muscle.

In a thirteenth embodiment, the electrical stimulation method can be used to stimulate the muscles associated with the knee joint. For example, the electrodes are positioned in electrical contact with tissue to stimulate a motor point of a patient's tibialis anterior, quadriceps, triceps surae, and/or hamstring muscles.

In a fourteenth embodiment, the electrical stimulation method can be used to stimulate the muscles associated with the hip and knee joints. For example, the electrodes are positioned in electrical contact with tissue to stimulate a motor point of a patient's quadriceps muscle group, vastus medialis muscle, gluteus medius muscle, gluteus minimus muscle, gluteus In a fifteenth embodiment, the electrical stimulation method can be used to stimulate the muscles associated with the knee joint. For example, the electrodes are positioned in electrical contact with tissue to stimulate a motor point of a patient's rectus femoris muscle, vastus lateralis muscle, vastus medialis muscle, biceps femoris muscle, semimembranosus muscle and/or semitendinosus muscle.

In yet a sixteenth embodiment, the electrical stimulation can be used to stimulate the muscles associated with the knee joint. For example, the first pair of electrodes are generally positioned on the patient's skin on the vastus medialis and upper quadricep, and the second pair is positioned on the hamstring and triceps surae muscles.

The series of electrical pulses applied to the one or more channels of electrodes may comprise a variety of different types of biphasic or triphasic pulse train patterns. For example, a plurality of cycles of a biphasic sequential or overlapping pulse train pattern may be used, in which a first phase of electrical pulses is applied to a first channel of electrodes, and a second phase of electrical pulses is applied to a second channel of electrodes. Using the biphasic sequential pulse train pattern, the second phase of electrical pulses commences after termination of the first phase of electrical pulses such that there is a time delay there between. Using the biphasic overlapping pulse train pattern, the second phase of electrical pulses commences before termination of the first phase of electrical pulses such that there is an overlap there between.

In another example, a plurality of cycles of a triphasic sequential or overlapping pulse train pattern may be used, in which a first phase of electrical pulses is applied to a first channel of electrodes, a second phase of electrical pulses is applied to a second channel of electrodes, and a third phase of electrical pulses is applied to the first channel of electrodes. Using the triphasic sequential pulse train pattern, the second phase of electrical pulses commences after termination of the first phase of electrical pulses such that there is a time delay there between, and, similarly, the third phase of electrical pulses commences after termination of the second phase of electrical pulses such that there is a time delay there between. Using the triphasic overlapping pulse train pattern, the second phase of electrical pulses commences before termination of the first phase of electrical pulses such that there is an overlap there between, and, similarly, the third phase of electrical pulses commences before termination of the second phase of electrical pulses such that there is an overlap there between.

In one aspect of the present invention, reduction of joint compression is shown by decreased co-contraction in opposing muscle groups associated with a joint as measured by muscle hardness and/or electromyography ("EMG") patterns. EMG is a technique for evaluating and recording the electrical activity of muscles at rest and while contracting. An electromyograph is used to produce an electromyogram, which is a graphic record of the electrical potential generated by muscle cells at rest and during contraction plotted over time. At rest, normal muscle tissue is electrically inactive. During contraction, normal muscle tissue is electrically active and produces action potentials that appear as peaks on the electromyogram. The electrical activity of multiple muscles can be tracked in relation to one another using EMG. When the EMG pattern for multiple muscles (agonist and antagonist) are compared, the length of time the action potential peaks overlap indicates the length of muscle co-contraction. In a preferred aspect, the EMG is integrated ("I-EMG") using commercially available hardware or software. The raw EMG signal is preferably rectified and integrated at a sample rate of 100-1000 Hz. The resulting data is then displayed as a value plotted on a graph.

A signal's frequency can be calculated in several possible ways, including via Fourier (and more easily implemented fast Fourier transform ("FFT")) transforms, measuring signal amplitude after band pass filtering, and via half waves. Thus, in another aspect, the reduction of joint compression is shown by decreased co-contraction in opposing muscle groups associated with a joint (agonist and antagonist) as measured by muscle hardness and/or FFT patterns. Higher mean frequencies and frequency spectrums indicates that the muscle is firing harder.

In another aspect of the present invention, reduction in joint compression is shown by decreased hypertonia measured using a tissue hardness and compliance measurement device. Hypertonia is abnormal increased muscle tone. Hypertonia of opposing muscles across a joint during movement or non-movement indicates joint compression. A tissue hardness and compliance measurement device typically comprises a metal probe approximately 1 cm$^2$ in area surrounded by a metal or plastic sleeve approximately 5 cm in diameter. Using a downward pressure, an examiner pushes the blunt metal probe perpendicular to the surface of the skin overlying the muscle to be tested. For example, compliance and tone of the right quadriceps femoris muscle can be measured by placing the tissue hardness and compliance measurement device above the right superior border of the patella at the thigh center line while a patient is seated. The probe does not penetrate the skin and only a light pressure by the examiner is needed. The tissue hardness and compliance measurement device measures the amount of deformation that occurs within the muscle (millimeter deflection) to a given unit of force. Muscle millimeter deflection can be measured when the muscle is relaxed to obtain a base-line muscle tone and compliance measurement. Muscle millimeter deflection can also be measured when the muscle is at varying levels of contraction. Varying levels of muscle contraction can be repeatedly obtained using a dynamometer. The higher the tone within the muscle, the less muscle millimeter deflection per unit of force. Muscle tone increases with the level of muscle contraction.

The electrical stimulation methods for reducing joint compression of the present invention are well-adapted to be used with other conventional therapies for overall joint health, including, but not limited to: implementing a supervised exercise program involving low-impact activities such as walking, swimming, and cycling; maintaining an ideal body weight; rest periods; applications of heat and cold; applications of light or lasers, application of pulsed and continuous magnetic fields, applications of electrical stimulation for pain control, nonsteroidal anti-inflammatory drugs (NSAIDS) or analgesics such as acetaminophen, ibuprofen, naproxen, or aspirin; tramadol; codeine; propoxyphene; glucosamine; chondroitin sulfate; salicylates; Cox-2 NSAIDS; surface application of capsaicin cream 0.25%; intra-articular injections of steroids, corticosteroids, or hyaluronic acid preparations; bracing, splinting, or orthotic treatments; and surgery including joint replacement and arthroscopic procedures.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

BRIEF DESCRIPTION OF THE DRAWINGS

The present invention will be described in greater detail in the following detailed description of the invention with reference to the accompanying drawings that form a part hereof, in which:

FIG. 7 shows the Visual Analog Scores of the five patients who received patterned neuromuscular stimulation as described in Example 2. FIG. 7A shows the patients' pain level, while

FIG. 11 shows the results of a "stand-up" test performed by the patients from Example 2.

DETAILED DESCRIPTION OF PREFERRED EMBODIMENT

Figure 1:
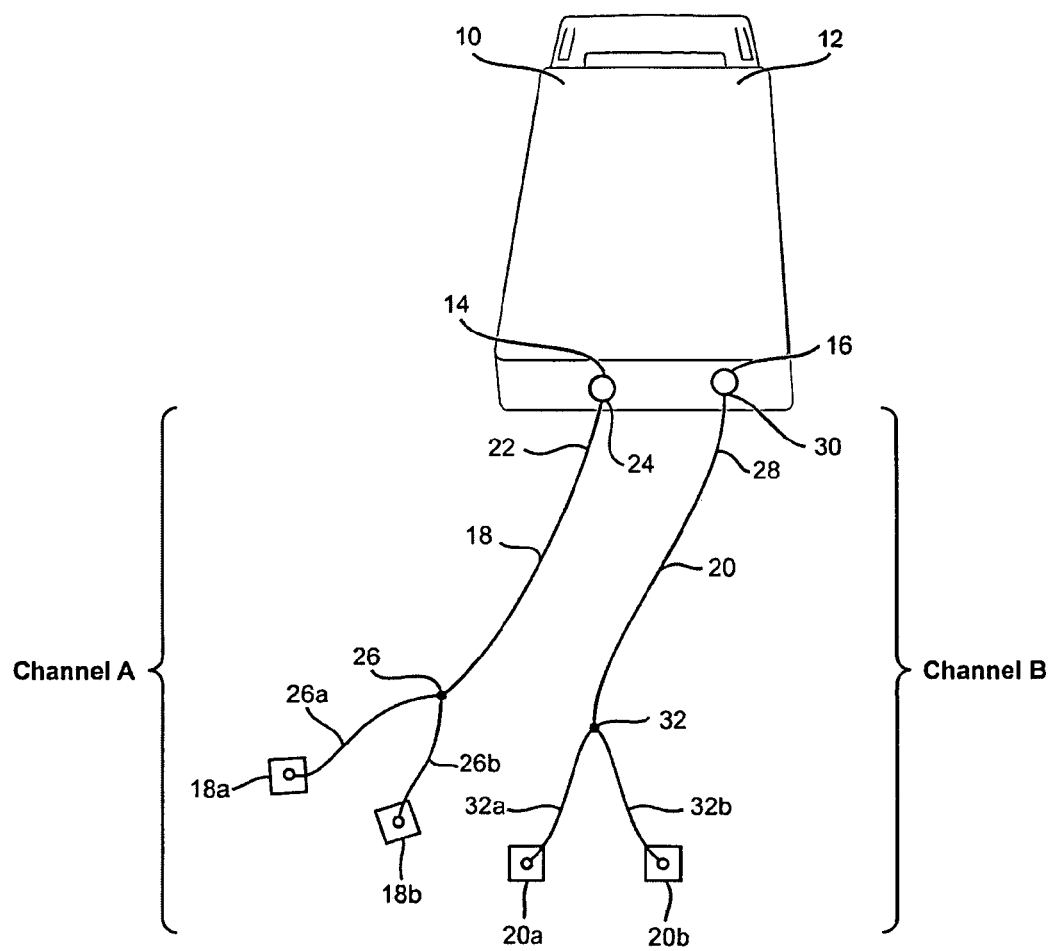
FIG. 1 is a block diagram of an electrical stimulation device that may be used in accordance with the method of the present invention.

The present invention is directed to an electrical stimulation method for reducing joint compression.

As used herein, the term "administration" refers to a method of giving an agent to a patient, where the method is, e.g., topical, oral, intravenous, transdermal, intraperitoneal, or intramuscular. The preferred method of administration can vary depending on various factors, e.g., the components of the pharmaceutical composition.

As used herein, "concurrent administration," "co-administration," or "co-treatment" includes administration of the agents or application of the electrical stimulation treatment method together, or before or after each other. The therapeutic agents co-administered with the electrical stimulation treatment methods may be administered by the same or different routes.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "therapeutically effective amount" as used herein, means that amount of an active agent which, alone or in combination with other drugs, provides a therapeutic benefit in the prevention, treatment, or management of joint compression. Different therapeutically effective amounts may be readily determined by those of ordinary skill in the art.

As used herein, the term "electrical stimulation" refers to the passing of various types of current to a patient through transcutaneous or percutaneous electrodes, and includes muscle activation by stimulation of the nerves innervating the sensory (cutaneous and position sensors) and muscle fibers associated with central pattern generator inputs or inhibitory mechanism and stimulation of motor efferent fibers which activate the muscles. The electrical stimulation used in the present invention is provided in a biphasic or triphasic pattern.

As used herein, the term "motor point" refers to an area of tissue that can be electrically stimulated by lower levels of electricity compared to surrounding areas. The motor point overlies the innervated zone of a muscle where the motor nerve endings are concentrated or where the nerve trunk enters the muscle. The motor point is often used as a placement site for surface electrodes used to stimulate the muscle.

As used herein, the term "tissue" refers to an aggregation of morphologically similar cells and associated intercellular matter acting together to perform one or more specific functions in the body, including epithelial, connective, muscle, and neural tissue.

As used herein, the term "treatment" refers to the treatment for reducing joint compression, in a patient, such as a mammal (particularly a human), which includes decreasing the length and intensity of co-contraction of opposing muscle groups associated with a joint as demonstrated by I-EMG, FFT, a combination thereof, or measuring muscle tone.

As used herein, the term "agonist muscle" broadly refers to a muscle that is resisted or counteracted by another muscle, the "antagonist muscle." Examples of agonist/antagonist muscle pairs include abductors/adductors, flexors/extensors, supinators/pronators, protractors/retractors, and evertors/inverters.

As used herein, the term "abductors" refers to muscles that generally cause movement away from the body centerline while "adductors" are muscles that generally cause movement toward the body centerline.

As used herein, the term "flexors" refers to muscles that generally reduce the angle of a joint, while "extensors" refers to muscles that increase the angle of the joint. For example, both the flexor carpi radialis and flexor carpi ulnaris are flexors of the wrist. The extensor carpi radialis longus, in conjunction with extensor carpi radialis brevis, is an extensor of the wrist.

As used herein, the term "pronator" refers to a muscle that causes the twisting movement of the wrist that turns the palm from facing front to facing back. The opposing movement, which turns the palm from facing back to facing front, is directed by a "supinator."

As used herein, the term "protractor" is a muscle that moves a part of the body anterior in the horizontal plane while a "retractor" muscle is involved in the reverse movement.

As used herein, the term "evertor" refers to a muscle involved in the twisting motion of the foot that turns the sole outward while the opposite movement of turning the sole inward is performed by an "inverter" muscle.

Referring to FIG. 1, an exemplary embodiment of an electrical stimulation device that may be used in accordance with the method of the present invention is designated generally as reference numeral 10. Electrical stimulation device 10 generally comprises an electronic control unit 12 with a plurality of output connectors 14, 16, which are connected to a plurality of output cables 18, 20 and associated electrode pairs 18a, 18b, and 20a, 20b, respectively. Although two output connectors 14, 16 are shown in FIG. 1, it should be understood that electronic control unit 12 may include any number of output connectors (such as one, two, six, or eight output connectors) in accordance with the present invention.

Output cables 18, 20 each comprise any suitable type of insulated conductive cable, such as a coaxial cable. In the illustrated embodiment, output cable 18 includes a back section 22 with a connector 24 (such as a male jack) that attaches to output connector 14, and a front section 26 that splits into a first split end 26a and a second split end 26b. Similarly, output cable 20 includes a back section 28 with a connector 30 (such as a male jack) that attaches to output connector 16, and a front section 32 that splits into a first split end 32a and a second split end 32b. Of course, it should be understood that each of the output cables 18, 20 could As can be seen in FIG. 1, electrodes 18a, 18b are attached to split ends 26a, 26b of output cable 18, respectively. Similarly, electrodes 20a, 20b are attached to split ends 32a, 32b of output cable 20, respectively. As such, output cable 18 and electrodes 18a, 18b together form a first output channel (referred to hereinafter as "channel A"), and output cable 20 and electrodes 20a, 20b together form a second output channel (referred to hereinafter as "channel B"). Although two channels are shown in FIG. 1, it should be understood that any number of channels (e.g., four, six, or eight channels) may be used in accordance with the present invention (provided, of course, that the number of channels corresponds to the number of output connectors of electronic control unit 12).

In the illustrated example, electrodes 18a and 20a each comprise a relative positive electrode, and electrodes 18b and 20b each comprise a relative negative electrode. As will be described in greater detail herein below, each of the electrical pulses applied to electrodes 18a, 18b and electrodes 20a, 20b may comprise, for example, a monophasic waveform (which has absolute polarity), a biphasic asymmetric waveform (which has relative polarity), or a biphasic symmetric waveform (which has no polarity). Thus, as used herein, the term "positive electrode" refers to a relative positive electrode and the term "negative electrode" refers to a relative negative electrode (regardless of whether the electrical pulse comprises a monophasic waveform, an asymmetric biphasic waveform, or a symmetric biphasic waveform which behaves like the relative positive or relative negative electrode during each phase of the waveform).

Electrodes 18a, 18b and 20a, 20b are each adapted to be positioned in electrical conduct with tissue of selected regions of a patient, as will be described in greater detail herein below with reference to FIG. 3A-3H. In the illustrated embodiment, each of electrodes 18a, 18b and 20a, 20b comprises a transcutaneous electrode having a surface electrode pad that may be placed on the skin of a patient. As is known in the art, each of electrodes 18a, 18b, and 20a, 20b may be formed of metal or some other physiologically acceptable conductive material and may take on a variety of different sizes and shapes. Of course, one or more of electrodes 18a, 18b and 20a, 20b may alternatively comprise a percutaneous electrode, such as a needle electrode, or any other type of suitable electrode in accordance with the present invention.

Electronic control unit 12 also includes internal circuitry (not shown) for selectively generating a series of electrical pulses in accordance with a procedure for treating joint compression. The series of electrical pulses generated by the circuitry are provided at output connectors 14, 16 and, as such, may be applied to a patient through channel A and/or channel B. The series of electrical pulses may comprise a variety of different types of pulse train patterns, such as: a plurality of cycles of a biphasic sequential pulse train pattern; a plurality of cycles of a biphasic overlapping pulse train pattern; a plurality of cycles of a triphasic sequential pulse train pattern; or a plurality of cycles of a triphasic overlapping pulse train pattern. Each of these pulse train patterns will be described in detail herein below with reference to FIGS. 2A-2D. One skilled in the art will understand that a variety of different circuit configurations may be used to generate the various pulse train patterns, such as the circuitry described in Palermo, U.S. Pat. No. 5,562,718, which is incorporated herein by reference.

A variety of different electrical stimulation devices may be used and/or adapted for use in accordance with the present invention. For example, one may incorporate the protocols disclosed herein into the Omnistim® FX$^2$ patterned electrical neuromuscular stimulator or the Omnistim® FX$^2$ Pro patterned electrical neuromuscular stimulator, both of which are commercially available from Accelerated Care Plus, 4850 Joule Street, Suite A-1, Reno, Nev. 89502. Of course, other types of electrical stimulation devices could also be used, which are generally available in the industry.

Referring now to FIGS. 2A-2D, examples of the various types of pulse train patterns that may be used in accordance with the present invention will now be described herein below. Preferably each pulse train pattern has a duration of 60 milliseconds to 200 milliseconds. The stimulation is timed such that there is a delay between pulse train patterns of 400 milliseconds to 1200 milliseconds. The delay is short enough not to create a startle response in the muscle and long enough to provide sufficient muscle relaxation and recovery. Preferably, the pulse train pattern is applied to the patient for a total treatment time of approximately 10 minutes to 60 minutes (and most preferably about 20 minutes to 30 minutes), as desired for a particular treatment.

Each of the pulse train patterns is comprised of a series of individual electrical pulses arranged into a particular pattern. Each of the electrical pulses may comprise either a monophasic or biphasic waveform, which may be, for example, asymmetric, symmetric, square, sinusoidal, and the like. Preferably, each of the electrical pulses comprises a biphasic asymmetric square wave having a pulse duration that ranges between 30 microseconds and 100 microseconds during the positive phase and a current amplitude that typically ranges between 25 milliamps and 140 milliamps.

Biphasic Sequential Pulse Train Pattern

Figure 2A:
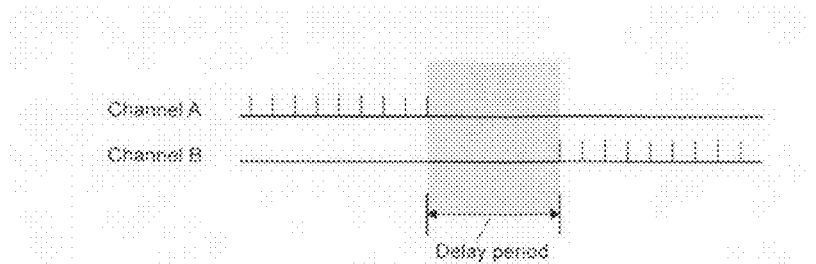
FIG. 2A is a timing diagram of a biphasic sequential pulse train pattern that may be applied to the output channels of the electrical stimulation device of FIG. 1.

Referring to FIG. 2A, electrical stimulation device 10 may be used to apply a plurality of cycles of a biphasic sequential pulse train pattern to a patient. In a typical biphasic sequential pulse train pattern, a first phase of electrical pulses is applied to channel A and a second phase of electrical pulses is applied to channel B with a delay period there between.

In the illustrated example, the first phase of electrical pulses is applied to channel A for approximately 60 milliseconds to 120 milliseconds (and most preferably about 100 milliseconds). At the conclusion of the first phase of electrical pulses, there is a delay period of approximately 0 milliseconds to 100 milliseconds (and most preferably about 80 milliseconds) before the second phase of electrical pulses is applied to channel B. Then, the second phase of electrical pulses is applied to channel B for approximately 60 milliseconds to 120 milliseconds (and most preferably about 100 milliseconds). The frequency of the individual electrical pulses in each phase is approximately 30 Hz to 100 Hz (and most preferably about 50 Hz).

Biphasic Overlapping Pulse Train Pattern

Figure 2B:
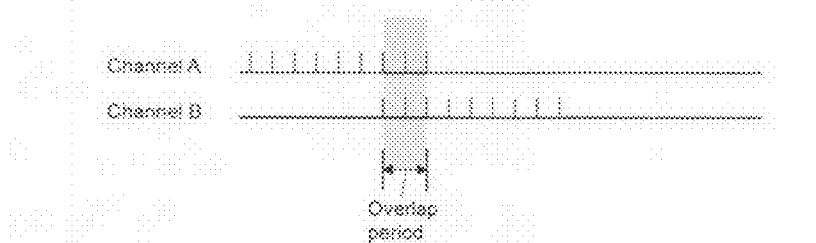
FIG. 2B is a timing diagram of a biphasic overlapping pulse train pattern that may be applied to the output channels of the electrical stimulation device of FIG. 1.

Referring to FIG. 2B, electrical stimulation device 10 may also be used to apply a plurality of cycles of a biphasic overlapping pulse train pattern to a patient. In a typical biphasic overlapping pulse train pattern, a first phase of electrical pulses is applied to channel A and a second phase of electrical pulses is applied to channel B with an overlap there between.

In the illustrated example, the first phase of electrical pulses is applied to channel A for approximately 60 milliseconds to 120 milliseconds (and most preferably about 100 milliseconds). When the first phase of electrical pulses has reached a time period of between 40 milliseconds and 100 milliseconds (and most preferably about 80 milliseconds), the second phase of electrical pulses is applied to channel B for approximately 60 milliseconds to 120 milliseconds (and most preferably about 100 milliseconds). Thus, there is an overlap of approximately 20 milliseconds to 80 milliseconds (and most preferably about 20 milliseconds) during which both channel A and channel B are providing electrical stimulation to the patient. The frequency of the individual electrical pulses in each phase is approximately 30 Hz to 100 Hz (and most preferably about 50 Hz).

Triphasic Sequential Pulse Train Pattern

Figure 2C:
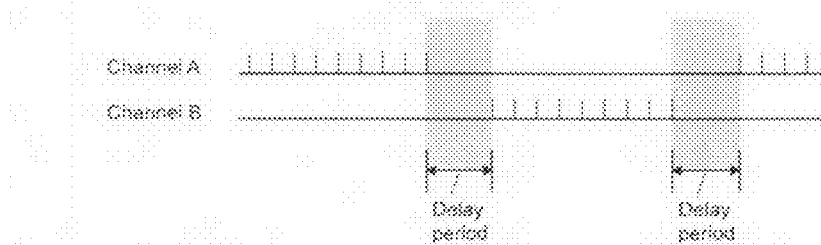
FIG. 2C is a timing diagram of a triphasic sequential pulse train pattern that may be applied to the output channels of the electrical stimulation device of FIG. 1.

Referring to FIG. 2C, electrical stimulation device 10 may also be used to apply a plurality of cycles of a triphasic sequential pulse train pattern to a patient. In a typical triphasic sequential pulse train pattern, a first phase of electrical pulses is applied to channel A, a second phase of electrical pulses is applied to channel B, and a third phase of electrical pulses is applied to channel A, wherein there is a delay period between the first and second phases of electrical pulses and another delay period between the second and third phases of electrical pulses.

In the illustrated example, the first phase of electrical pulses is applied to channel A for approximately 60 milliseconds to 120 milliseconds (and most preferably about 100 milliseconds). At the conclusion of the first phase of electrical pulses, there is a delay period of approximately 0 milliseconds to 100 milliseconds (and most preferably about 80 milliseconds) before the second phase of electrical pulses is applied to channel B. Then, the second phase of electrical pulses is applied to channel B for approximately 60 milliseconds to 120 milliseconds (and most preferably about 100 milliseconds). At the conclusion of the second phase of electrical pulses, there is a delay period of approximately 0 milliseconds to 100 milliseconds (and most preferably about 80 milliseconds) before the third phase of electrical pulses is applied to channel A. Then, the third phase of electrical pulses is applied to channel A for approximately 36 milliseconds to 72 milliseconds (and most preferably about 60 milliseconds). The frequency of the individual electrical pulses in each phase is approximately 30 Hz to 100 Hz (and most preferably about 50 Hz).

Triphasic Overlapping Pulse Train Pattern

Figure 2D:
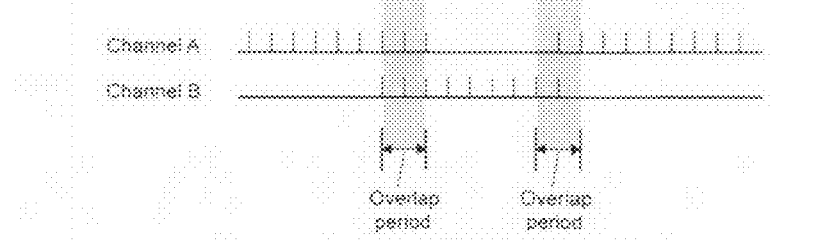
FIG. 2D is a timing diagram of a triphasic overlapping pulse train pattern that may be applied to the output channels of the electrical stimulation device of FIG. 1.

Referring to FIG. 2D, electrical stimulation device 10 may also be used to apply a plurality of cycles of a triphasic overlapping pulse train pattern to a patient. In a typical triphasic overlapping pulse train pattern, a first phase of electrical pulses is applied to channel A, a second phase of electrical pulses is applied to channel B, and a third phase of electrical pulses is applied to channel A, wherein there is an overlap period between the first and second phases of electrical pulses and another overlap period between the second and third phases of electrical pulses.

In the illustrated example, the first phase of electrical pulses is applied to channel A for approximately 60 milliseconds to 120 milliseconds (and most preferably about 100 milliseconds). When the first phase of electrical pulses has reached a time period of between 40 milliseconds and 100 milliseconds (and most preferably about 80 milliseconds), the second phase of electrical pulses is applied to channel B for approximately 60 milliseconds to 120 milliseconds (and most preferably about 100 milliseconds). Thus, there is an overlap period of approximately 20 milliseconds to 80 milliseconds (and most preferably about 20 milliseconds) during which both channel A and channel B are providing electrical stimulation to the patient. When the second phase of electrical pulses has reached a time period of between 40 milliseconds and 100 milliseconds (and most preferably about 80 milliseconds), the third phase of electrical pulses is applied to channel A for approximately 36 milliseconds to 72 milliseconds (and most preferably about 60 milliseconds) (i.e., the third phase of electrical pulses has a shorter time duration than that of the first phase of electrical pulses). Thus, there is an overlap of approximately 20 milliseconds to 72 milliseconds (and most preferably about, 20 milliseconds) during which both channel B and channel A are providing electrical stimulation to the patient. The frequency of the individual electrical pulses in each phase is approximately 30 Hz to 100 Hz (and most preferably about 50 Hz).

Figure 3A:
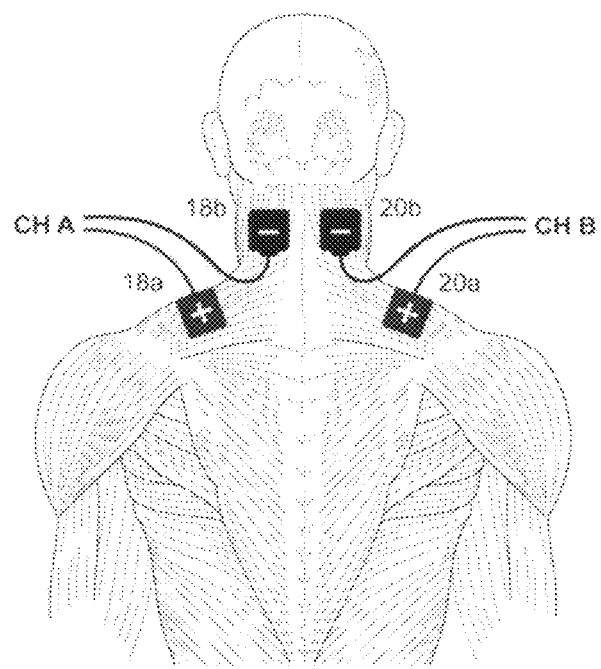
FIG. 3A illustrates a method for treating joint compression in a patient by applying electrical stimulation in accordance with a first exemplary embodiment of the present invention.
Figure 3B:
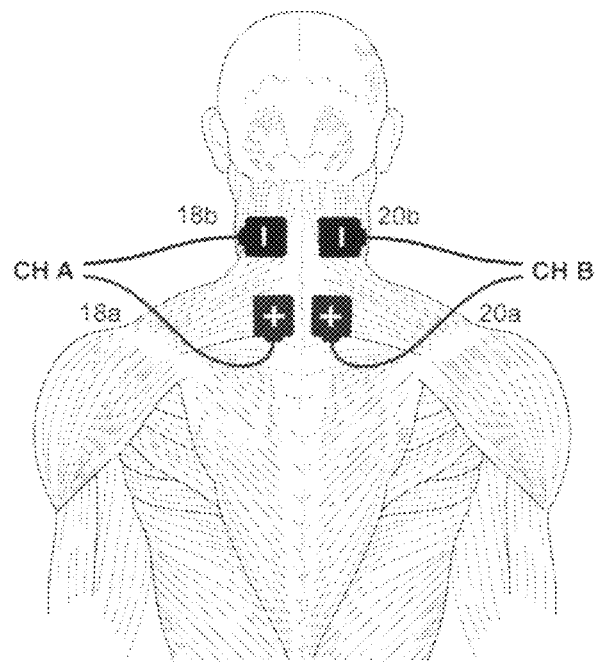
FIG. 3B illustrates a method for treating joint compression in a patient by applying electrical stimulation in accordance with a second exemplary embodiment of the present invention.
Figure 3C:
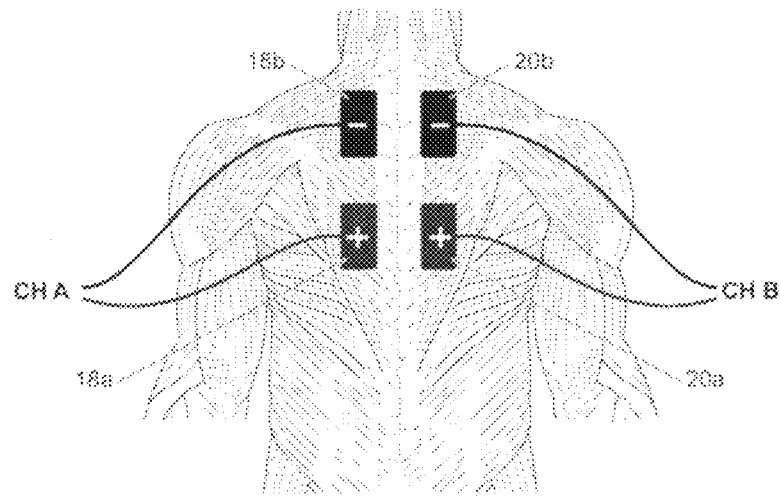
FIG. 3C illustrates a method for treating joint compression in a patient by applying electrical stimulation in accordance with a third exemplary embodiment of the present invention.
Figure 3D:
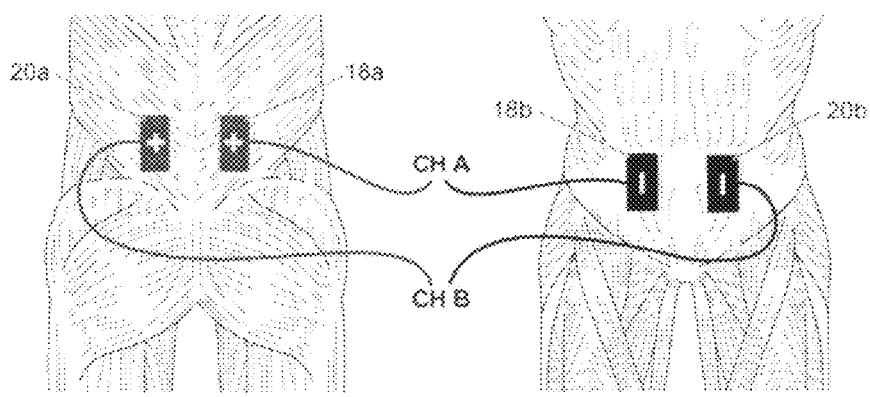
FIG. 3D illustrates a method for treating joint compression in a patient by applying electrical stimulation in accordance with a fourth exemplary embodiment of the present invention.
Figure 3E:
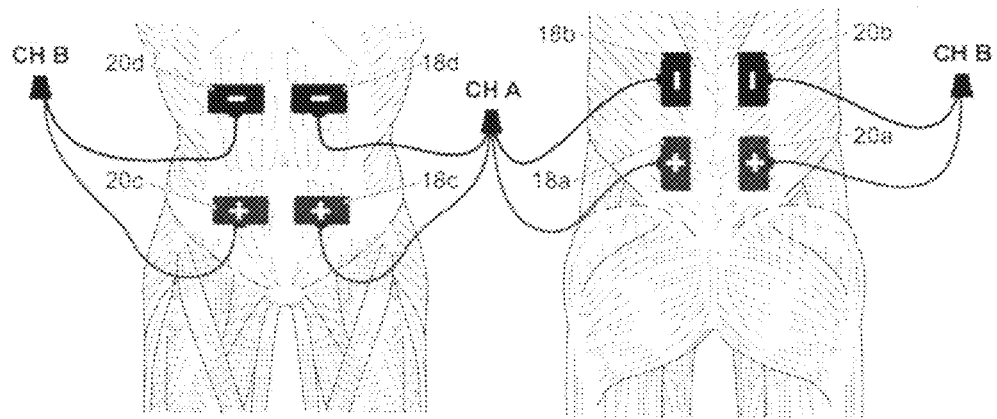
FIG. 3E illustrates a method for treating joint compression in a patient by applying electrical stimulation in accordance with a fifth exemplary embodiment of the present invention.
Figure 3F:
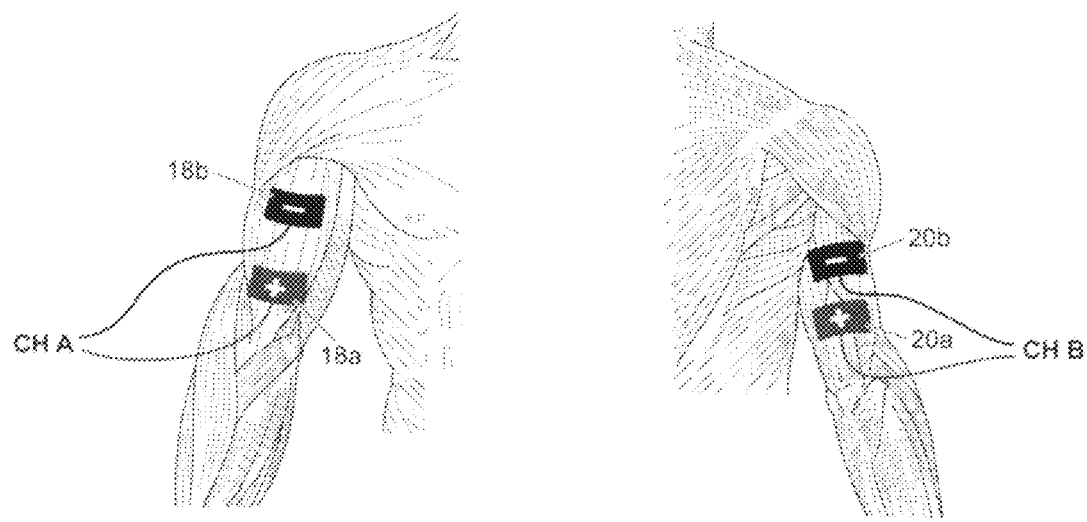
FIG. 3F illustrates a method for treating joint compression in a patient by applying electrical stimulation in accordance with a sixth exemplary embodiment of the present invention.
Figure 3G:
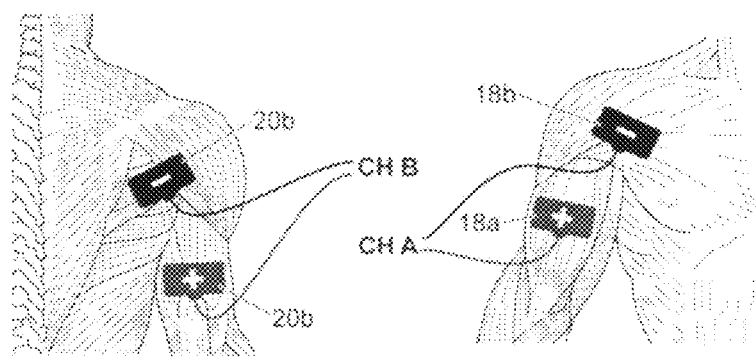
FIG. 3G illustrates a method for treating joint compression in a patient by applying electrical stimulation in accordance with a seventh exemplary embodiment of the present invention.
Figure 3H:
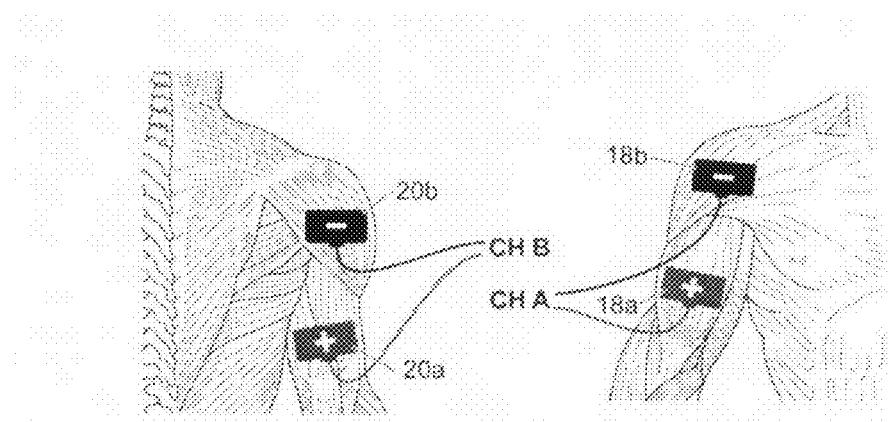
FIG. 3H illustrates a method for treating joint compression in a patient by applying electrical stimulation in accordance with an eighth exemplary embodiment of the present invention.
Figure 3I:
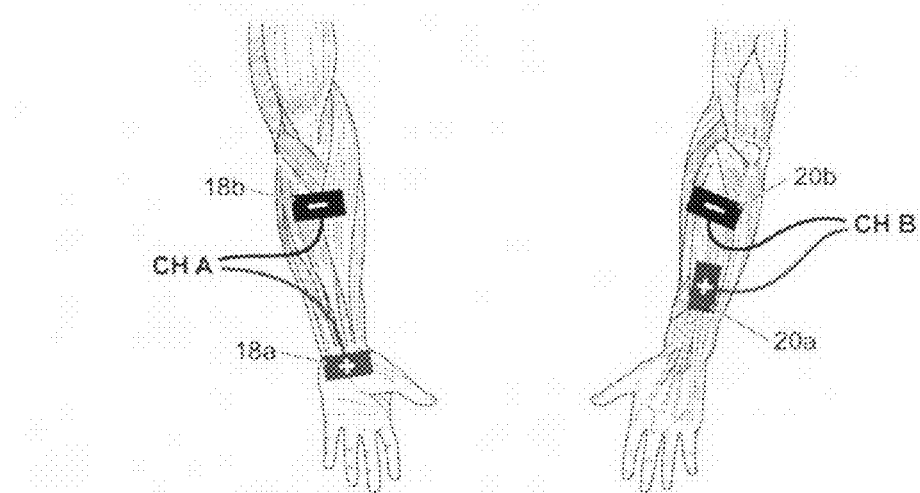
FIG. 3I illustrates a method for treating joint compression in a patient by applying electrical stimulation in accordance with a ninth exemplary embodiment of the present invention.
Figure 3J:
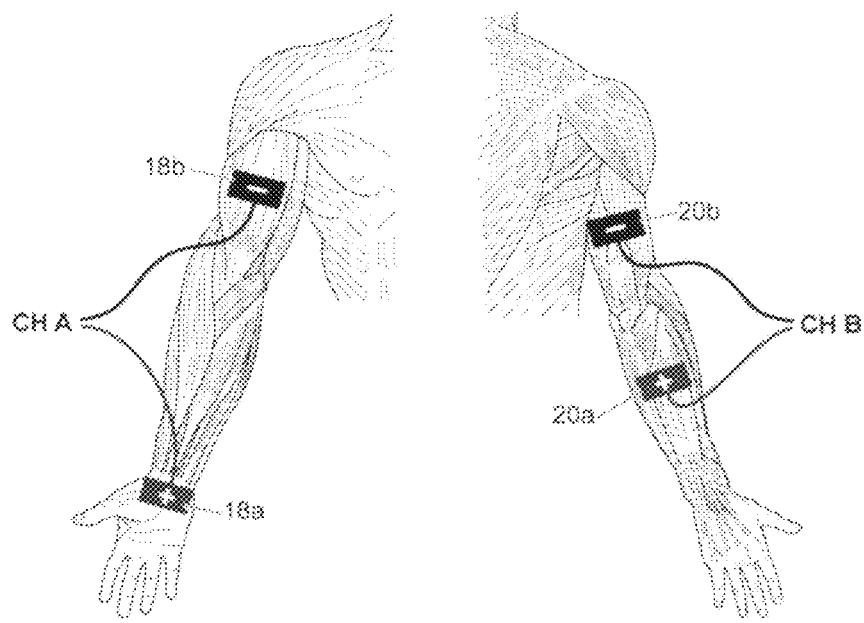
FIG. 3J illustrates a method for treating joint compression in a patient by applying electrical stimulation in accordance with a tenth exemplary embodiment of the present invention.
Figure 3K:
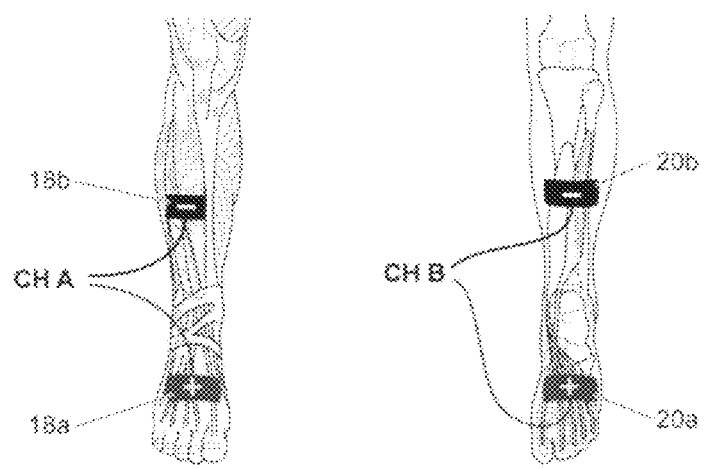
FIG. 3K illustrates a method for treating joint compression in a patient by applying electrical stimulation in accordance with an eleventh exemplary embodiment of the present invention.
Figure 3L:
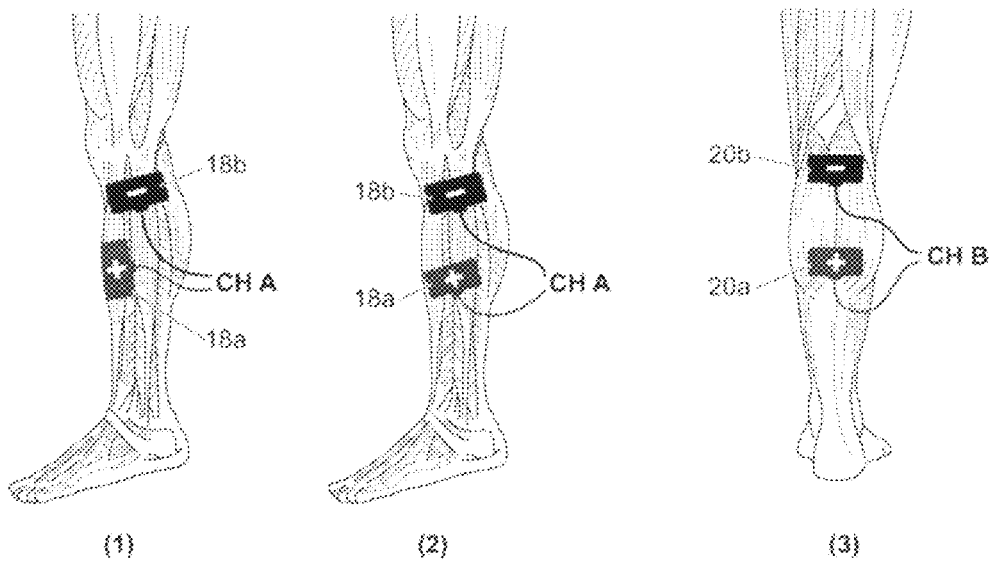
FIG. 3L illustrates a method for treating joint compression in a patient by applying electrical stimulation in accordance with a twelfth exemplary embodiment of the present invention.
Figure 3M:
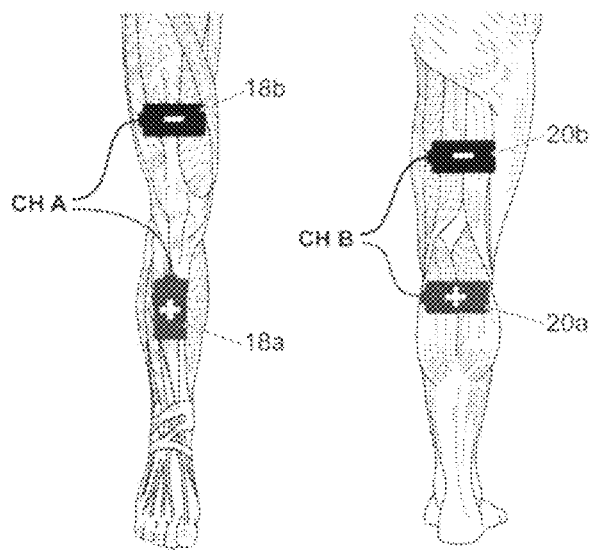
FIG. 3M illustrates a method for treating joint compression in a patient by applying electrical stimulation in accordance with a thirteenth exemplary embodiment of the present invention.
Figure 3N:
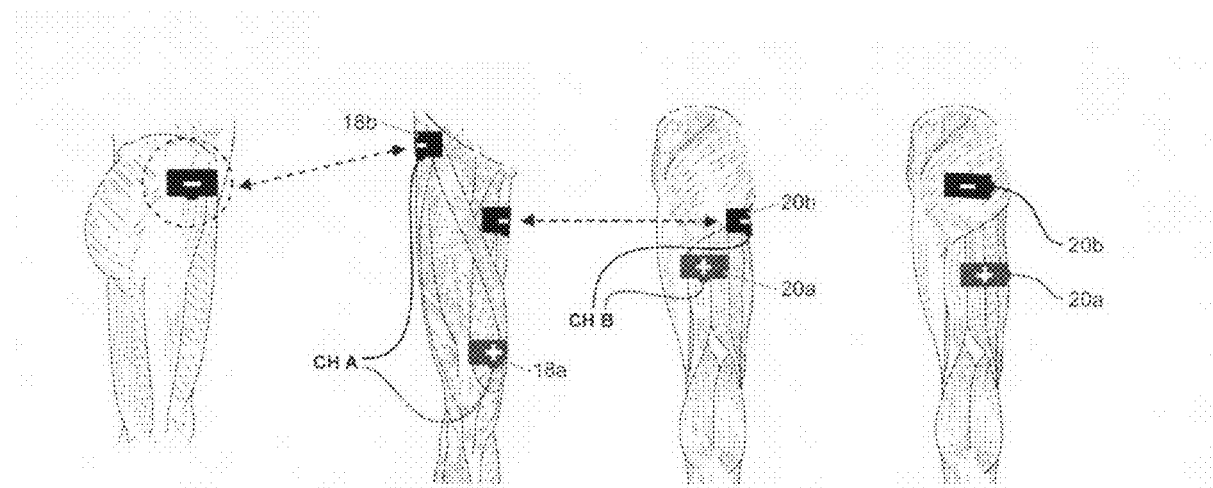
FIG. 3N illustrates a method for treating joint compression in a patient by applying electrical stimulation in accordance with a fourteenth exemplary embodiment of the present invention.
Figure 3O:
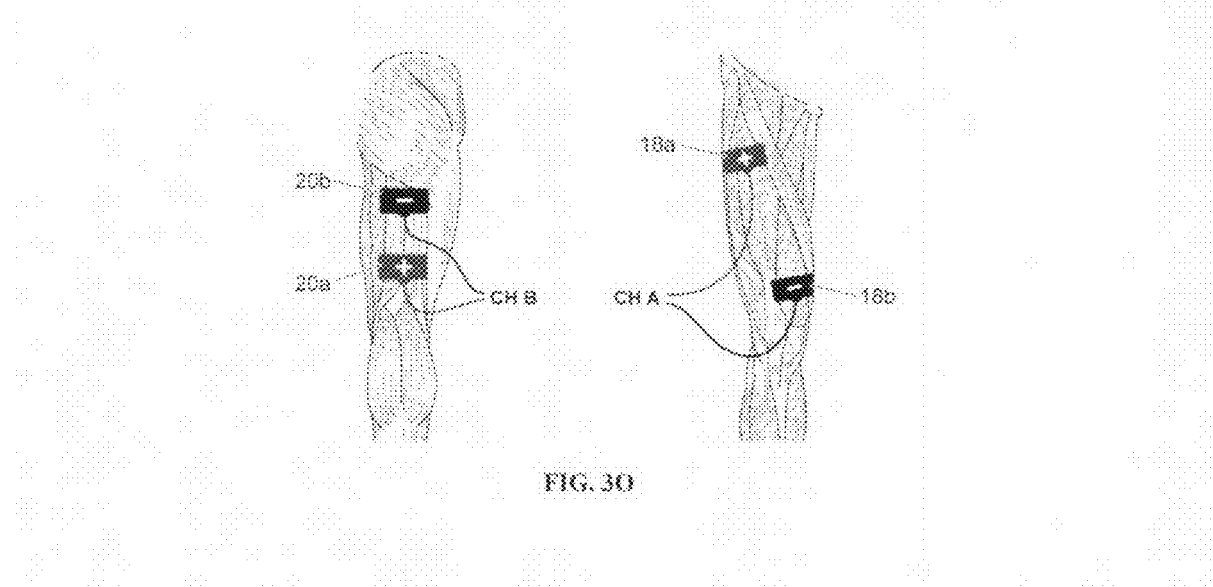
FIG. 3O illustrates a method for treating joint compression in a patient by applying electrical stimulation in accordance with a fifteenth exemplary embodiment of the present invention.

Referring now to FIG. 3A-3O, electrodes 18a, 18b and 20a, 20b are each adapted to be positioned in electrical contact with tissue of selected regions of a patient. The selected regions are preferably those that will assist in programming the central pattern generators associated with the muscles associated with opposing joint movement such as agonist/antagonist muscle pairs in the neck, trunk, shoulder, arm, wrist, hand, hip, thigh, lower leg, ankle, and foot of the patient that control intervertebral, elbow, shoulder, wrist, ankle, knee, and hip joint movement. In the present invention, the muscle contractions produced by the pulse train patterns provide afferent inputs or efferent stimulation that assist in retraining the central nervous system and spinal motor loops to promote normal muscle function and decrease co-contraction. Importantly, it is theorized that biphasic and triphasic pulse train pattern stimulation assists in retraining central pattern generators when functional pulse train patterns cannot be created either because of the difficulty in assessing the muscle groups involved or the research is too time consuming and costly.

The electrical stimulation methods for reducing joint compression of the present invention are well-adapted to be used with other conventional therapies for overall joint health, including, but not limited to: implementing a supervised exercise program involving low-impact activities such as walking, swimming, and cycling; maintaining an ideal body weight; rest periods; applications of heat and cold; applications of light or laser; application of pulsed or continuous magnetic fields; application of electrostimulation for pain management; nonsteroidal anti-inflammatory drugs (NSAIDS) or analgesics such as acetaminophen, ibuprofen, naproxen, or aspirin; tramadol; codeine; propoxyphene; glucosamine; chondroitin sulfate; salicylates; Cox-2 NSAIDS; surface application of capsaicin cream 0.25%; intra-articular injections of steroids, corticosteroids, or hyaluronic acid preparations; bracing, splinting, or orthotic treatments; and surgery including joint replacement and arthroscopic procedures.

While several exemplary embodiments of the present invention are discussed below, those skilled in the art will readily appreciate that various modifications may be made to these embodiments, and the invention is not limited to the specific electrode placements and pulse train patterns described therein.

First Exemplary Embodiment

In a first exemplary embodiment of the present invention, as generally illustrated in FIG. 3A, a pair of electrodes is positioned in electrical contact with the patient's tissue in order to provide electrical stimulation to one or more of the muscles associated with intervertebral and shoulder joint movement. A second pair of electrodes is positioned bilaterally in a similar manner.

More specifically, as shown in FIG. 3A, a two-channel system is used to apply electrical stimulation to agonist/antagonist muscles involved in neck intervertebral and shoulder joint movement. For the first channel, a first electrode 18a is positioned in electrical contact with tissue to stimulate a motor point of the patient's upper trapezius muscle. Most preferably, first electrode 18a comprises a surface electrode that is positioned on the patient's skin along the midpoint of the upper trapezium. A second electrode 18b is positioned is electrical contact with tissue to stimulate a motor point of the patient's cervical paraspinal muscles. Most preferably, second electrode 18b comprises a surface electrode that is positioned on the patient's skin in the posterior neck region just lateral to one or more of cervical vertebrae, most preferably near the C1, C2, C3, and/or C4 cervical vertebrae. For the second channel, a second pair of electrodes 20a, 20b is provided bilaterally in a similar position as generally illustrated in FIG. 3A.

In this exemplary embodiment, the pulse train pattern comprises a biphasic overlapping pulse train pattern having the following parameters:
Pulse duration of individual electrical pulses: 50-70 microseconds
Current amplitude of individual electrical pulses: 20-70 milliamps
Duration of first phase: 100 milliseconds
Duration of overlap: 20 milliseconds
Duration of second phase: 100 milliseconds
Frequency of pulse train pattern: 1.6 Hz
Total treatment time: 20 minutes
Total number of treatments: 18 over six weeks
Frequency of individual electrical pulses (in each phase): 50 Hz Second Exemplary Embodiment In a second exemplary embodiment of the present invention, as generally illustrated in FIG. 3B, two pairs of electrodes are positioned in electrical contact with the patient's tissue in order to provide electrical stimulation to one or more of the muscles associated with intervertebral and shoulder joint movement More specifically, as shown in FIG. 3B, a two-channel system is used to apply electrical stimulation to agonist/antagonist muscles involved in neck intervertebral and shoulder joint movement. For the first channel, a first electrode 118a is positioned in electrical contact with tissue to stimulate a motor point of the patient's lower cervical and upper thoracic paraspinal muscles. Most preferably, first electrode 18a comprises a surface electrode that is positioned on the patient's skin along the midpoint of the upper trapezius just lateral to the spinal cord, most preferably near the C6, C7, T1, T2, T3, and/or T4 cervical and thoracic vertebrae. A second electrode 18b is positioned in electrical contact with tissue to stimulate a motor point of the patient's cervical paraspinal muscles. Most preferably, second electrode 18b comprises a surface electrode that is positioned on the patient's skin in the posterior neck region just lateral to one or more cervical vertebrae, most preferably near the C1, C2, C3, and/or C4 cervical vertebrae. For the second channel, a second pair of electrodes 20a, 20b is provided bilaterally in a similar position as generally illustrated in FIG. 3B.

In this exemplary embodiment, the pulse train pattern comprises a biphasic overlapping pulse train pattern having the following parameters:
Pulse duration of individual electrical pulses: 50-70 microseconds
Current amplitude of individual electrical pulses: 20-70 milliamps
Duration of first phase: 100 milliseconds
Duration of overlap: 20 milliseconds
Duration of second phase: 100 milliseconds
Frequency of pulse train pattern: 1.6 Hz
Total treatment time: 20 minutes
Total number of treatments: 18 (over six weeks)
Frequency of individual electrical pulses (in each phase): 50 Hz Third Exemplary Embodiment In a third exemplary embodiment of the present invention, as generally illustrated in FIG. 3C, two pairs of electrodes are positioned in electrical contact with the patient's tissue in order to provide electrical stimulation to one or more of the muscles associated with intervertebral joint movement.

More specifically, as shown in FIG. 3C, a two channel system is used to apply electrical stimulation to agonist/antagonist muscles involved in upper and mid-back intervertebral joint movement including the erector spinae and trapezius muscles. For the first channel, a first electrode 18a is positioned in electrical contact with tissue to stimulate a motor point of the patient's thoracic paraspinal muscles. Most preferably, first electrode 18a comprises a surface electrode that is positioned on the patient's skin just lateral to one or more thoracic vertebrae, most preferably near the T3, T4, T5, T6, T7, T8, and/or T9 thoracic vertebrae. A second electrode 18b is positioned in electrical contact with tissue to stimulate a motor point of the patient's upper thoracic paraspinal muscles. Most preferably, second electrode 18a comprises a surface electrode that is positioned on the patient's skin along the midpoint of the upper trapezius just lateral to the spinal cord, most preferably near the C7, T1, T2, T3, and/or T4 cervical and thoracic vertebrae. For the second channel, a second pair of electrodes 20a, 20b is provided bilaterally in a similar position as generally illustrated in FIG. 3C.

In this exemplary embodiment, the pulse train pattern comprises a biphasic overlapping pulse train pattern having the following parameters:
 Pulse duration of individual electrical pulses: 50-70 microseconds
 Current amplitude of individual electrical pulses: 20-70 milliamps
 Duration of first phase: 100 milliseconds
 Duration of overlap: 20 milliseconds
 Duration of second phase: 100 milliseconds
 Frequency of pulse train pattern: 1.6 Hz
 Total treatment time: 20 minutes
 Total number of treatments: 36
 Frequency of individual electrical pulses (in each phase): 50 Hz Fourth Exemplary Embodiment In a fourth exemplary embodiment of the present invention, as generally illustrated in FIG. 3D, a pair of electrodes is positioned in electrical contact with the patient's tissue in order to provide electrical stimulation to one or more of the muscles associated with intervertebral joint movement. A second pair of electrodes is positioned bilaterally in a similar manner.

More specifically, as shown in FIG. 3D, a two-channel system is used to apply electrical stimulation to agonist/antagonist muscles involved in lumbar intervertebral joint movement. For the first channel, a first electrode 18a is positioned in electrical contact with tissue to stimulate a motor point of the patient's lower back muscles. Most preferably, first electrode 18a comprises a surface electrode that is positioned posteriorly on the patient's skin in the lower back region over the lower paraspinal muscles just lateral to one or more of the lower thoracic and/or lumbar vertebrae, most preferably near the L1, L2, L3, L4, and/or L5 lumbar vertebrae. A second electrode 18b is positioned in electrical contact with tissue to stimulate a motor point of the patient's abdominal muscles. Most preferably, second electrode 18b comprises a surface electrode that is positioned anteriorly on the patient's skin at about the level of the umbilicus, about half-way between the anterior superior iliac spine ("ASIS") and the anterior midline over the combined abdominal muscle. For the second channel, a second pair of electrodes 20a, 20b is provided bilaterally in a similar position as generally illustrated in FIG. 3D.

In this exemplary embodiment, the pulse train pattern comprises a triphasic overlapping pulse train pattern having the following parameters:
 Pulse duration of individual electrical pulses: 50-70 microseconds
 Current amplitude of individual electrical pulses: 20-90 milliamps
 Duration of first phase: 200 milliseconds
 Duration of overlap: 40 milliseconds
 Duration of second phase: 200 milliseconds
 Duration of overlap: 40 milliseconds
 Duration of third phase: 120 milliseconds
 Frequency of pulse train pattern: 0.67 Hz
 Frequency of individual electrical pulses (in each phase): 50 hertz
 Total treatment time: 20 minutes
 Total number of treatments: 18 over six weeks Fifth Exemplary Embodiment In a fifth exemplary embodiment of the present invention, as generally illustrated in FIG. 3E, four pairs of electrodes are positioned in electrical contact with the patient's tissue in order to provide electrical stimulation to one or more of the muscles associated with intervertebral joint movement. Two channels may be used with a bifurcating cable as illustrated in FIG. 3E.

More specifically, as shown in FIG. 3E, a two-channel system is used to apply electrical stimulation to agonist/antagonist muscles involved in trunk intervertebral joint movement. For the first channel, a first electrode 18a is positioned in electrical contact with tissue to stimulate a motor point of the patient's upper lumbar and upper abdominal muscles. Most preferably, first electrode 18a comprises a surface electrode that is positioned posteriorly on the patient's skin in the lower back region over the multifidus muscle, just lateral to one or more of the lower thoracic and/or lumbar vertebrae, most preferably near the L1, L2, L3, L4, and/or L5 lumbar vertebrae. A second electrode 18b of the first channel is also placed posteriorly on the patient's skin in the lower back region over the multifidus muscle, just lateral to one or more of the lower thoracic and/or lumbar vertebrae, most preferably near the T9, T10, T11, T12, L1, L2, and/or L3 lumbar vertebrae. A third electrode 18c and a fourth electrode 18d are placed over the same side of the abdominal muscles at the same vertebral level to stimulate the patient's lower abdominal muscles. Another set of four electrodes 20a, 20b, 20c, and 20d is provided bilaterally in a similar position as generally illustrated in FIG. 3E.

In this exemplary embodiment, the pulse train pattern comprises a triphasic overlapping pulse train pattern having the following parameters:
 Pulse duration of individual electrical pulses: 50-70 microseconds
 Current amplitude of individual electrical pulses: 20-70 milliamps
 Duration of first phase: 200 milliseconds
 Duration of overlap: 40 milliseconds
 Duration of second phase: 200 milliseconds
 Duration of overlap: 40 milliseconds
 Duration of third phase: 120 milliseconds
 Frequency of pulse train pattern: 0.67 Hz
 Frequency of individual electrical pulses (in each phase): 50 Hz
 Total treatment time: 20 minutes
 Total number of treatments: 18 over six weeks Sixth Exemplary Embodiment In a sixth exemplary embodiment of the present invention, also generally illustrated in FIG. 3F, two pairs of electrodes are positioned in electrical contact with the patient's tissue in order to provide electrical stimulation to one or more of the muscles associated with elbow flexion/extension.

More specifically, as shown in FIG. 3F, a two-channel system is used to apply electrical stimulation to muscles of the upper arm. For the first channel, a first electrode 18a and a second electrode 18b are positioned in electrical contact with tissue to stimulate motor points of the patient's biceps brachii muscles (flex the forearm at the elbow). Most preferably, first electrode 18a comprises a surface electrode that is positioned on the patient's skin on the anterior side of the upper arm just above the insertion of the biceps brachii muscles. Most preferably, second electrode 18b comprises a surface electrode that is positioned on the patient's skin on the anterior side of the upper arm just below the origin of the biceps brachii muscles.

For the second channel, a first electrode 20a and a second electrode 20b are positioned in electrical contact with tissue to stimulate motor points of the patient's triceps brachii muscles (extend the forearm at the elbow). Most preferably, first electrode 20a comprises a surface electrode that is positioned on the patient's skin on the posterior side of the upper arm above the insertion of the triceps brachii muscles. Most preferably, second electrode 20b comprises a surface electrode that is positioned on the patient's skin on the posterior side of the upper arm below the origin of the triceps brachii muscles.

During treatment, the first and second channels are positioned on the right or left arm, and a patterned pulse train is applied to the upper arm as discussed more fully below. It will be appreciated that the muscles involved in elbow flexion/extension may be bilaterally stimulated when the electrical stimulation device contains at least four channels. Alternatively, two electrical stimulation devices can be used for bilateral stimulation: one to stimulate the right upper arm, and one to stimulate the left upper arm.

In this exemplary embodiment, the pulse train pattern comprises a triphasic overlapping pulse train pattern having the following parameters:

Pulse duration of individual electrical pulses: 50-70 microseconds
Current amplitude of individual electrical pulses: 30-70 milliamps
Duration of first phase: 100 milliseconds
Duration of overlap between first and second phases: 20 milliseconds
Duration of second phase: 100 milliseconds
Duration of overlap between second and third phases: 20 milliseconds
Duration of third phase: 60 milliseconds
Frequency of pulse train pattern: 0.67 Hz
Total treatment time: 20 minutes
Total number of treatments: 18 during six weeks
Frequency of individual electrical pulses (in each phase): 50 Hz Seventh Exemplary Embodiment In a seventh exemplary embodiment of the present invention, as generally illustrated in FIG. 3G, two pairs of electrodes are positioned in electrical contact with the patient's tissue in order to provide electrical stimulation to one or more of the muscles involved in the internal and external rotation of the shoulder.

More specifically, as shown in FIG. 3G, a two channel system is used to apply electrical stimulation to agonist/antagonist muscles involved in shoulder movement. For the first channel, a first pair of electrodes 18a, 18b is positioned to provide simulation to muscles involved in the internal rotation of the shoulder. A first electrode 18a is positioned in electrical contact with tissue to stimulate a motor point of the patient's biceps brachii muscle. Most preferably, first electrode 18a comprises a surface electrode that is positioned on the patient's skin near the midpoint of the biceps brachii muscle. A second electrode 18b is positioned in electrical contact with tissue to stimulate a motor point of the patient's pectoralis major and anterior deltoid muscle. Most preferably, second electrode 18b comprises a surface electrode that is positioned anteriorly on the patient's skin just above the axilla.

For the second channel, a second pair of electrodes 20a, 20b is provided to stimulate the muscles involved in the external rotation of the shoulder. A first electrode 20a is positioned in electrical contact with tissue to stimulate a motor point of the patient's triceps brachii muscle. Most preferably, first electrode 20a comprises a surface electrode that is positioned near the midpoint of the triceps brachii. A second electrode 20b is positioned in electrical contact with tissue to stimulate a motor point of the patient's infraspinatus teres minor and the posterior deltoid muscle. Most preferably, second electrode 20b comprises a surface electrode that is positioned posteriorly on the patient's skin just above the underarm.

During treatment, the first and second channels are positioned on the right or left arm, and a patterned pulse train is applied as discussed more fully below. It will be appreciated that the muscles involved in shoulder rotation may be bilaterally stimulated when the electrical stimulation device contains at least four channels. Alternatively, two electrical stimulation devices can be used for bilateral stimulation: one to simulate the right shoulder, and one to stimulate the left shoulder.

In this exemplary embodiment, the pulse train pattern comprises a triphasic overlapping pulse train pattern having the following parameters:

Pulse duration of individual electrical pulses: 50-70 microseconds
Current amplitude of individual electrical pulses: 30-70 milliamps
Duration of first phase: 100 milliseconds
Duration of overlap: 20 milliseconds
Duration of second phase: 100 milliseconds
Duration of overlap: 20 milliseconds
Duration of third phase: 60 milliseconds
Frequency of pulse train pattern: 0.67 Hz
Total treatment time: 20 minutes
Total number of treatments: 18 over six weeks
Frequency of individual electrical pulses (in each phase): 50 Hz Eighth Exemplary Embodiment In an eighth exemplary embodiment of the present invention, as generally illustrated in FIG. 3H, two pairs of electrodes are positioned in electrical contact with the patient's tissue in order to provide electrical stimulation to one or more of the muscles involved in shoulder and elbow flexion/extension.

More specifically, as shown in FIG. 3H, a two-channel system is used to apply electrical stimulation to agonist/antagonist muscles involved in shoulder and elbow extension/flexion. For the first channel, a first electrode 18a is positioned in electrical contact with tissue to stimulate a motor point of the patient's biceps brachii muscle. Most preferably, first electrode 18a comprises a surface electrode that is positioned on the patient's skin near the midpoint of the biceps brachii muscle. A second electrode 18b is positioned in electrical contact with tissue to stimulate a motor point of the patient's anterior deltoid muscle. Most preferably, second electrode 18b comprises a surface electrode that is positioned anteriorly on the patient's skin just above the axilla.

For the second channel, a first electrode 20a is positioned in electrical contact with tissue to stimulate a motor point of the patient's triceps brachii muscle. Most preferably, first electrode 20a comprises a surface electrode that is positioned near the distal end of the triceps brachii. A second electrode 20b is positioned in electrical contact with tissue to stimulate a motor point of the patient's posterior deltoid muscle. Most preferably, second electrode 20b comprises a surface electrode that is positioned posteriorly on the patient's skin just above the axilla.

During treatment, the first and second channels are positioned on the right or left arm, and a patterned pulse train is applied as discussed more fully below. It will be appreciated that the muscles involved in shoulder rotation may be bilaterally stimulated when the electrical stimulation device contains at least four channels. Alternatively, two electrical stimulation devices can be used for bilateral stimulation: one to simulate the right shoulder, and one to stimulate the left shoulder.

In this exemplary embodiment, the pulse train pattern comprises a triphasic overlapping pulse train pattern having the following parameters:

Pulse duration of individual electrical pulses: 50-70 microseconds
Current amplitude of individual electrical pulses: 30-70 milliamps
Duration of first phase: 100 milliseconds
Duration of overlap: 20 milliseconds
Duration of second phase: 100 milliseconds
Duration of overlap: 20 milliseconds
Duration of third phase: 60 milliseconds
Frequency of pulse train pattern: 0.67 Hz
Total treatment time: 20 minutes
Total number of treatments: 18 (over six weeks)
Frequency of individual electrical pulses (in each phase): 50 Hz Ninth Exemplary Embodiment In a ninth exemplary embodiment of the present invention, also generally illustrated in FIG. 3I, two pairs of electrodes are positioned in electrical contact with the patient's tissue in order to provide electrical stimulation to one or more of the muscles associated with wrist flexion/extension, wrist pronation/supination, and/or finger flexion/extension. The treated muscles include the flexor digitorum superficialis, flexor carpi radialis, flexor carpi ulnaris, extensor digitorum. extensor digiti minimi muscle, extensor carpi ulnaris, extensor carpi radialis longus, and/or extensor carpi radialis brevis.

More specifically, as shown in FIG. 3I, a two-channel system is used to apply electrical stimulation to muscles of the wrist and fingers. For the first channel, a first electrode 18a is positioned in electrical contact with tissue of the patient's proximal palmar surface to stimulate motor points of the patient's intrinsic hand muscles. Most preferably, first electrode 18a comprises a surface electrode that is positioned on the patient's skin across the thenar and the hypothenar eminence on the palmar/anterior side of the forearm arm at the base of the wrist just below the wrist crease. A second electrode 18b is positioned in electrical contact with tissue to stimulate motor points of the patient's volar-surface, proximal forearm muscles. Most preferably, second electrode 18b comprises a surface electrode that is positioned on the patient's skin on the palmar/anterior side of the lower arm just below the elbow joint.

For the second channel, a first electrode 20a is positioned in electrical contact with tissue to stimulate a motor point of the patient's extensor digitorum muscle (extends medial four digits at metacarpophalangeal joints, and extends the hand at the wrist) and pollicis muscles. Most preferably, first electrode 20a comprises a surface electrode that is positioned on the patient's skin on the dorsal/posterior side of the lower arm on the distal one-third between the wrist crease and the elbow joint. A second electrode 20b is positioned in electrical contact with a tissue to stimulate motor points of the patient's proximal extensor muscles of the forearm. Most preferably, second electrode 20b comprises a surface electrode that is positioned on the patient's skin on the dorsal/posterior side of the lower arm just below the elbow joint.

During treatment, the first and second channels are positioned on the right or left arm, and a patterned pulse train is applied to the arm and wrist as discussed more fully below. It will be appreciated that the muscles involved in wrist and finger extension/flexion may be bilaterally stimulated when the electrical stimulation device contains at least four channels. Alternatively, two electrical stimulation devices can be used for bilateral stimulation: one to stimulate the right wrist and fingers, and one to stimulate the left wrist and fingers.

In this exemplary embodiment, the pulse train pattern comprises a triphasic overlapping pulse train pattern having the following parameters:

Pulse duration of individual electrical pulses: 50-70 microseconds
Current amplitude of individual electrical pulses: 30-70 milliamps
Duration of first phase: 100 milliseconds
Duration of overlap between first and second phases: 20 milliseconds
Duration of second phase: 100 milliseconds
Duration of overlap between second and third phases: 20 milliseconds
Duration of third phase: 60 milliseconds
Frequency of pulse train pattern: 0.67 Hz
Total treatment time: 20 minutes
Total number of treatments: 18 during six weeks
Frequency of individual electrical pulses (in each phase): 50 Hz Tenth Exemplary Embodiment In a tenth exemplary embodiment of the present invention, also generally illustrated in FIG. 3J, two pairs of electrodes are positioned in electrical contact with the patient's tissue in order to provide electrical stimulation to one or more of the muscles involved in wrist and elbow movement.

More specifically, as shown in FIG. 3J, a two-channel system is used to apply electrical stimulation to agonist/antagonist muscles involved in wrist and elbow movement. For the first channel, a first pair of electrodes 18a, 18b provide stimulation to the anterior portion of the arm. A first electrode 18a is positioned in electrical contact with tissue of the proximal palmar surface to stimulate a motor point of the patient's intrinsic hand muscles. Most preferably, first electrode 18a comprises a surface electrode that is positioned on the patient's skin across the thenar and hypothenar eminence of the palmar/anterior side of the forearm at the base of the wrist just below the wrist crease. A second electrode 18b is positioned in electrical contact with tissue to stimulate a motor point of the patient's biceps brachii muscles, the median nerve, and the ulnar nerve. Most preferably, second electrode 18b comprises a surface electrode that is positioned on the patient's skin anterior and medially (to capture the median and ulnar nerve bundle) near the midpoint of the biceps brachii muscles.

For the second channel, a second pair of electrodes 20a, 20b is provided to stimulate the posterior muscles of the arm. A first electrode 20a is positioned in electrical contact with tissue to stimulate a motor point of the patient's proximal extensor muscles of the forearm. Most preferably, first electrode 20a comprises a surface electrode that is positioned on the patient's skin on the dorsal/posterior side of the lower arm just below the elbow joint. A second electrode 20b is positioned in electrical contact with tissue to stimulate a motor point of the patient's triceps brachii muscles. Most preferably, second electrode 20b comprises a surface electrode that is positioned on the patient's skin on the posterior side of the arm near the midpoint of the triceps brachii muscles.

During treatment, the first and second channels are positioned on the right or left arm, and a patterned pulse train is applied to the arm and wrist as discussed more fully below. It will be appreciated that the muscles involved in arm movement may be bilaterally stimulated when the electrical stimulation device contains at least four channels. Alternatively, two electrical stimulation devices can be used for bilateral stimulation: one to stimulate the right arm, and one to stimulate the left arm.

In this exemplary embodiment, the pulse train pattern comprises a triphasic overlapping pulse train pattern having the following parameters:

Pulse duration of individual electrical pulses: 50-70 microseconds

Current amplitude of individual electrical pulses: 30-70 milliamps

Duration of first phase: 100 milliseconds

Duration of overlap between first and second phases: 20 milliseconds

Duration of second phase: 100 milliseconds

Duration of overlap between second and third phases: 20 milliseconds

Duration of third phase: 60 milliseconds

Frequency of pulse train pattern: 0.67 Hz

Total treatment time: 20 minutes

Total number of treatments: 18 during six weeks

Frequency of individual electrical pulses (in each phase): 50 Hz

Eleventh Exemplary Embodiment

In an eleventh exemplary embodiment of the present invention, as generally illustrated in FIG. 3K, two pairs of electrodes are positioned in electrical contact with the patient's tissue in order to provide electrical stimulation to one or more of the muscles associated with toe and ankle dorsiflexion (or extension) and flexion (or plantar flexion).

More specifically, as shown in FIG. 3K, a two-channel system is used to apply electrical stimulation to agonist/antagonist muscles involved in toe and ankle extension/flexion. For the first channel, a first electrode 18a is positioned in electrical contact with tissue to stimulate a motor point of the patient's extensor digitorum brevis muscle (extends the joints of the proximal phalanges of toes 1-4). Most preferably, first electrode 18a comprises a surface electrode that is positioned on the patient's skin on the dorsum of the foot over the first four metatarsal bones. A second electrode 18b is positioned in electrical contact with tissue to stimulate a motor point of the patient's tibialis anterior (extends foot at the ankle), extensor digitorum longus (extends toes 2-5 and the foot at the ankle), and/or extensor hallucis longus (extends toe 1 and the foot at the ankle) muscles. Most preferably, second electrode 18b comprises a surface electrode that is positioned on the patient's skin at the anterior lateral mid-shaft of the leg over the mid-tibialis anterior and the approximate mid-belly of the extensor digitorum longus and extensor hallucis longus muscles.

For the second channel, a first electrode 20a is positioned in electrical contact with tissue to stimulate motor points of the patient's intrinsic foot muscles. Most preferably, first electrode 20a comprises a surface electrode that is positioned on the patient's skin on the sole of the foot at the anterior one-third junction to include the abductor hallucis. A second electrode 20b is positioned in electrical contact with tissue to stimulate motor points of the patient's tibialis posterior (flexes the foot at the ankle) and flexor hallucis muscles. Most preferably, second electrode 20b comprises a surface electrode that is positioned on the patient's skin on the posterior distal one-third of the lower leg.

During treatment, the first and second channels are positioned on the right or left leg, and a patterned pulse train is applied to the leg as discussed more fully below. It will be appreciated that the muscles involved in toe and ankle extension/flexion may be bilaterally stimulated when the electrical stimulation device contains at least four channels. Alternatively, two electrical stimulation devices can be used for bilateral stimulation: one to stimulate the right leg, and one to stimulate the left leg.

In this exemplary embodiment, the pulse train pattern comprises a triphasic overlapping pulse train pattern having the following parameters:

Pulse duration of individual electrical pulses: 50-70 microseconds

Current amplitude of individual electrical pulses: 30-70 milliamps

Duration of first phase: 200 milliseconds

Duration of overlap between first and second phase: 40 milliseconds

Duration of second phase: 200 milliseconds

Duration of overlap between second and third phase: 40 milliseconds

Duration of third phase: 120 milliseconds

Frequency of pulse train pattern: 0.67 Hz

Total treatment time: 20 minutes

Total number of treatments: 18 during six weeks

Frequency of individual electrical pulses (in each phase): 50 Hz

Twelfth Exemplary Embodiment

In a twelfth exemplary embodiment of the present invention, generally illustrated in FIG. 3L, two pairs of electrodes are positioned in electrical contact with the patient's tissue in order to provide electrical stimulation to one or more of the muscles associated with ankle dorsiflexion and plantar flexion and ankle eversion/inversion.

More specifically, as shown in FIG. 3L, a two-channel system is used to apply electrical stimulation to muscles involved in ankle dorsiflexion and plantar flexion and/or ankle inversion/eversion. For the first channel (panel 1 of FIG. 3L), a first electrode 18a is positioned in electrical contact with tissue to stimulate a motor point of the patient's lower portion of the tibialis anterior muscle. Most preferably, first electrode 18a comprises a surface electrode that is positioned on the patient's skin over the mid-belly of the tibialis anterior muscle. A second electrode 18b is positioned in electrical contact with tissue to stimulate a motor point of the patient's proximal tibialis anterior muscle. Most preferably, second electrode 18b comprises a surface electrode that is positioned on the patient's skin inferior to the fibular head.

Alternatively, for the first channel (panel 2 of FIG. 3L), a first electrode 18a is positioned in electrical contact with tissue to stimulate motor points of the patient's anterior and lateral muscles of the leg. Most preferably, first electrode 18a comprises a surface electrode that is positioned on the patient's skin at the mid-belly of the tibialis anterior as well as the peroneus muscles. A second electrode 18b is positioned in electrical contact with tissue to stimulate a motor point of the patient's proximal tibialis anterior muscle. Most preferably, second electrode 18b comprises a surface electrode that is positioned on the patient's skin inferior to the fibular head.

For the second channel (panel 3 of FIG. 3L), a first electrode 20a and a second electrode 20b are positioned in electrical contact with tissue to stimulate motor points of the patient's triceps surae (comprised of the gastrocnemius medial head (which plantar flexes the foot at the ankle), the gastrocnemius lateral head (which plantar flexes foot at the ankle), and/or the soleus muscle (which plantar flexes the foot at the ankle)). Most preferably, first electrode 20a comprises a surface electrode that is positioned on the patient's skin directly over the junction of the gastrocnemius and soleus muscles. Most preferably, second electrode 20b comprises a surface electrode that is positioned on the patient's skin posteriorly just inferior to the popliteal fossa over the tibial nerve and the two heads of the gastrocnemius muscle.

During treatment, the first and second channels are positioned on the right or left leg, and a patterned pulse train is applied to the leg as discussed more fully below. It will be appreciated that the muscles involved in ankle dorsiflexion and plantar flexion and/or ankle inversion/eversion may be bilaterally stimulated when the electrical stimulation device contains at least four channels. Alternatively, two electrical stimulation devices can be used for bilateral stimulation: one to stimulate the right leg, and one to stimulate the left leg.

In this exemplary embodiment, the pulse train pattern comprises a triphasic overlapping pulse train pattern having the following parameters:

Pulse duration of individual electrical pulses: 50-70 microseconds

Current amplitude of individual electrical pulses: 30-70 milliamps

Duration of first phase: 200 milliseconds

Duration of overlap between first and second phase: 40 milliseconds

Duration of second phase: 200 milliseconds

Duration of overlap between second and third phase: 40 milliseconds

Duration of third phase: 120 milliseconds

Frequency of pulse train pattern: 0.67 Hz

Total treatment time: 20 minutes

Total number of treatments: 18 during six weeks

Frequency of individual electrical pulses (in each phase): 50 Hz

Thirteenth Exemplary Embodiment

In a thirteenth exemplary embodiment of the present invention, also generally illustrated in FIG. 3M, two pairs of electrodes are positioned in electrical contact with the patient's tissue in order to provide electrical stimulation to one or more of the muscles associated with movement in the lower extremities.

More specifically, as generally shown in FIG. 3M, a two-channel system is used to apply electrical stimulation to muscles involved in leg movement. For the first channel, a first electrode 18a is positioned in electrical contact with tissue to stimulate a motor point of the patient's proximal tibialis anterior muscle. Most preferably, first electrode 18a comprises a surface electrode that is positioned on the patient's skin on the anterior side of the leg and inferior to the fibular head. A second electrode 18b is positioned in electrical contact with tissue to stimulate a motor point near the midpoint of a patient's quadriceps muscles. Most preferably, second electrode 18b comprises a surface electrode that is positioned on the patient's skin on the anterior side of the leg just above the knee.

For the second channel, a first electrode 20a is positioned in electrical contact with tissue to stimulate a motor point of the patient's triceps surae muscles. Most preferably, first electrode 20a comprises a surface electrode that is positioned on the patient's skin on the posterior side of the lower leg near the midpoint of the gastrocnemius muscle. The second electrode 20b is positioned in electrical contact with a tissue to stimulate a motor point of the patient's mid-hamstrings. Most preferably, second electrode 20b comprises a surface electrode that is positioned on the patient's skin on the distal one third of the posterior side of the leg.

During treatment, the first and second channels are positioned on the right or left leg, and a patterned pulse train is applied to the leg as discussed more fully below. It will be appreciated that the muscles involved in leg movement may be bilaterally stimulated when the electrical stimulation device contains at least four channels. Alternatively, two electrical stimulation devices can be used for bilateral stimulation: one to stimulate the right leg, and one to stimulate the left leg.

In this exemplary embodiment, the pulse train pattern comprises a triphasic overlapping pulse train pattern having the following parameters:

Pulse duration of individual electrical pulses: 50-100 microseconds

Current amplitude of individual electrical pulses: 30-90 milliamps

Duration of first phase: 200 milliseconds

Duration of overlap between first and second phases: 40 milliseconds

Duration of second phase: 200 milliseconds

Duration of overlap between second and third phases: 40 milliseconds

Duration of third phase: 120 milliseconds

Frequency of pulse train pattern: 0.67 Hz

Total treatment time: 20 minutes

Total number of treatments: 18 during six weeks

Frequency of individual electrical pulses (in each phase): 50 Hz

Fourteenth Exemplary Embodiment

In a fourteenth exemplary embodiment of the present invention, generally illustrated in FIG. 3N, a pair of electrodes is positioned in electrical contact with the patient's tissue in order to provide electrical stimulation to one or more of the muscles associated with hip abduction and knee extension as well as hip adduction and knee flexion (stabilization).

More specifically, as generally shown in FIG. 3N, a two-channel system is used to apply electrical stimulation to muscles involved in hip abduction/adduction and knee extension/flexion. For the first channel, a first electrode 18a is positioned in electrical contact with the quadricep muscles, and in particular to stimulate the motor point of the vastus medialis, which functions as an extensor of the knee. A second electrode 18b is positioned in electrical contact with tissue to stimulate the gluteus medius, gluteus minimus, and tensor faciae latae. Preferably, the second electrode 18b is positioned about midway between the iliac crest and the greater trochanter. For the second channel, a first electrode 20a is positioned in electrical contact with tissue to stimulate the patient's hamstring muscles (biceps femoris, semitendinosus, and/or semimembraneous muscles). A second electrode 20b is positioned in electrical contact with tissue to stimulate the adductor magnus, adductor longus, adductor brevis, and medial hamstring muscles.

The far right panel of FIG. 3N shows the hip extensor alternative placement: In the second channel, a first electrode 20a is positioned in electrical contact with tissue to stimulate the adductor magnus, adductor longus, adductor brevis and medial hamstring muscles. A second electrode 20*b* is positioned in electrical contact with tissue to stimulate the midbelly of the gluteus maximus.

During treatment, the first and second channels are positioned on the right or left leg, and a patterned pulse train is applied to the leg as discussed more fully below. It will be appreciated that the muscles involved in hip abduction/adduction and knee extension/flexion may be bilaterally stimulated when the electrical stimulation device contains at least four channels. Alternatively, two electrical stimulation devices can be used for bilateral stimulation: one to simulate the right leg, and one to stimulate the left leg.

In this exemplary embodiment, the pulse train pattern comprises a triphasic overlapping pulse train pattern having the following parameters:

Pulse duration of individual electrical pulses: 50-200 microseconds
Current amplitude of individual electrical pulses: 30-140 milliamps
Duration of first phase: 200 milliseconds
Duration of overlap between first and second phase: 40 milliseconds
Duration of second phase: 200 milliseconds
Duration of overlap between second and third phase: 40 milliseconds
Duration of third phase: 120 milliseconds
Frequency of pulse train pattern: 0.67 Hz
Total treatment time: 20 minutes
Total number of treatments: 18 during six weeks
Frequency of individual electrical pulses (in each phase): 50 Hz Fifteenth Exemplary Embodiment In an eighth exemplary embodiment of the present invention, also generally illustrated in FIG. 3O, two pairs of electrodes are positioned in electrical contact with the patient's tissue in order to provide electrical stimulation to one or more of the muscles associated with knee extension/flexion as a treatment for joint compression in the lower extremities. More specifically, as generally shown in FIG. 3O, a two-channel system is used to apply electrical stimulation to muscles involved in knee extension/flexion. For the first channel, a first electrode 18*a* is positioned in electrical contact with tissue to stimulate a motor point of the patient's rectus femoris (extends leg at the knee) and vastus lateralis (extends leg at the knee) muscles. Most preferably, first electrode 18*a* comprises a surface electrode that is positioned on the patient's skin on the proximal one third of the anterior side of the upper leg. A second electrode 18*b* is positioned in electrical contact with tissue to stimulate the motor point of the patient's vastus medialis muscle (extends the leg at the knee). Most preferably, second electrode 18*b* comprises a surface electrode that is positioned on the patient's skin on the anterior medial side of the upper leg just above the knee.

For the second channel, a first electrode 20*a* is positioned in electrical contact with tissue to stimulate a motor point of the patient's distal portion of the biceps femoris muscle (flexes the leg at the knee), semimembranosus muscle (flexes the leg at the knee), and/or semitendinosus muscle (flexes the leg at the knee). Most preferably, first electrode 20*a* comprises a surface electrode that is positioned on the patient's skin on the posterior side of the upper leg just above the knee. A second electrode 20*b* is positioned in electrical contact with a tissue to stimulate a motor point of the patient's proximal portion of the biceps femoris, semimembranosus, and/or semitendinosus muscles. Most preferably, second electrode 20*b* comprises a surface electrode that is positioned on the patient's skin on the proximal one third of the posterior side of the upper leg.

During treatment, the first and second channels are positioned on the right or left leg, and a patterned pulse train is applied to the leg as discussed more fully below. It will be appreciated that the muscles involved in knee flexion/extension may be bilaterally stimulated when the electrical stimulation device contains at least four channels. Alternatively, two electrical stimulation devices can be used for bilateral stimulation: one to stimulate the right leg, and one to stimulate the left leg.

In this exemplary embodiment, the pulse train pattern comprises a triphasic overlapping pulse train pattern having the following parameters:

Pulse duration of individual electrical pulses: 50-200 microseconds
Current amplitude of individual electrical pulses: 30-140 milliamps
Duration of first phase: 200 milliseconds
Duration of overlap between first and second phases: 40 milliseconds
Duration of second phase: 200 milliseconds
Duration of overlap between second and third phases: 40 milliseconds
Duration of third phase: 120 milliseconds
Frequency of pulse train pattern: 0.67 Hz
Total treatment time: 20 minutes
Total number of treatments: 18 during six weeks
Frequency of individual electrical pulses (in each phase): 50 Hz

EXAMPLE 1

Measuring Muscle Hardness

In this example, muscle hardness was correlated to I-EMG ratios. More specifically, fourteen healthy female subject were seated in a fixed position, and postured with the hip joint at a 60 degree angle, with the body trunk fixed by a belt. The arms were positioned on the sides of the body and the hands were positioned on the anterior edge of the chair. Tissue compliance (hardness) was measured 22 cm above the right superior border patella at the thigh center line using the ACP Tissue Compliance Meter. EMG pads were positioned on the right quadricepts femoris muscle. One electrode was positioned 9 cm above the right superior border paella, and the other electrode was positioned a center of the thigh line between 9 to 17 cm above the right superior patella with the ground in the center.

Six tests were performed on each subject. For the first test, the subject's knee was flexed at a 60 degree angle with no load. The EMG was measured for 10 seconds, and the tissue compliance (hardness) was measured three times during the ten-second interval.

For the remaining five tests, the subject's knee was flexed at a 60 degree angle and a motorized dynamometer was used to apply a load of 10, 20, 30, 40, and 60 pounds. The EMG was measured when the applied load was reached during each contraction for a period of 10 seconds while the contraction was maintained The tissue compliance (hardness) was measured three times during the ten-second interval while the EMG was being measured.

Figure 4:
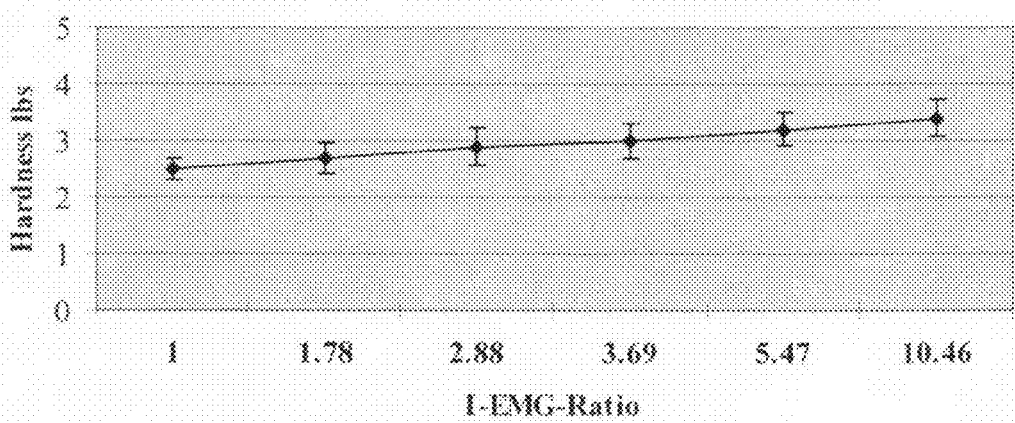
FIG. 4 illustrates the correlation between muscle hardness and the I-EMG ratio. The Spearman's correlation coefficient was $R=0.618$, $p<0.01$, $N=14$. This demonstrates that the measurement of muscle hardness is directly correlated to the I-EMG ratio between the agonist and antagonist muscles.

As shown in FIG. 4, the tissue compliance (hardness, lbs) was plotted as a function of I-EMG. (mV) Increasing I-EMG resulted in increasing tissue hardness (tissue compliance).

Thus, this figure shows that muscle contraction can be indirectly measured by the I-EMG of the subject.

Figure 5:
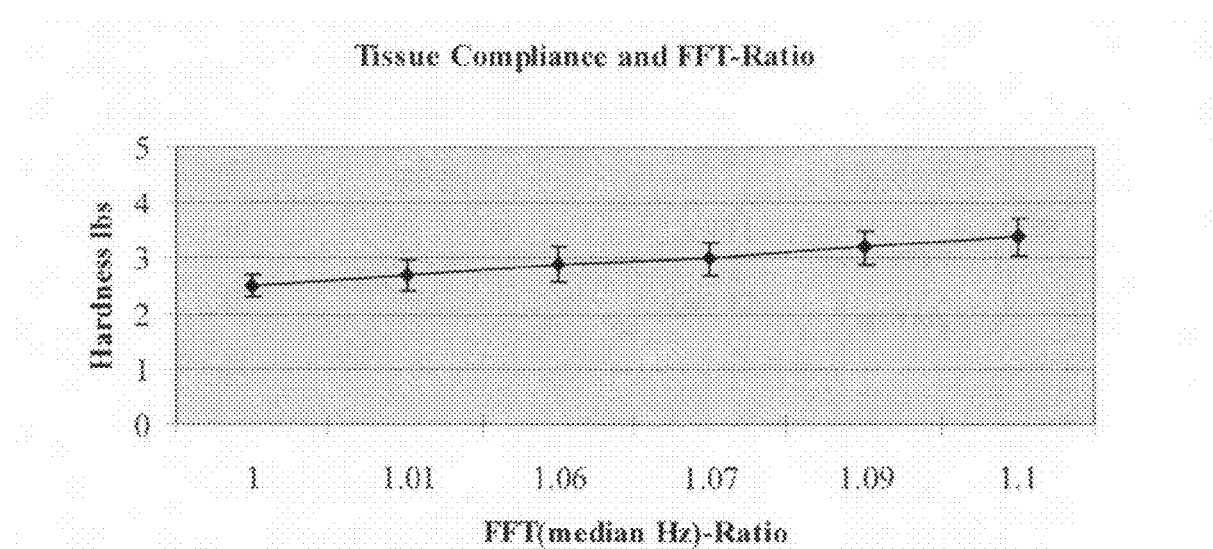
FIG. 5 illustrates the relationship between muscle hardness and the FFT ratio. The Spearman's correlation coefficient was $R=0.447$, $p<0.01$, $N=14$. This demonstrates that the measurement of muscle hardness is directly correlated to the FFT ratio between the agonist and antagonist muscles.

As shown in FIG. 5, the tissue compliance (hardness, lbs) was plotted as a function of FFT (median Hz). Increasing tissue compliance resulted in increasing FFT. Thus, this figure shows that muscle contraction can be indirectly measured by the shift in the median FFT frequency of the subject.

Figure 6:
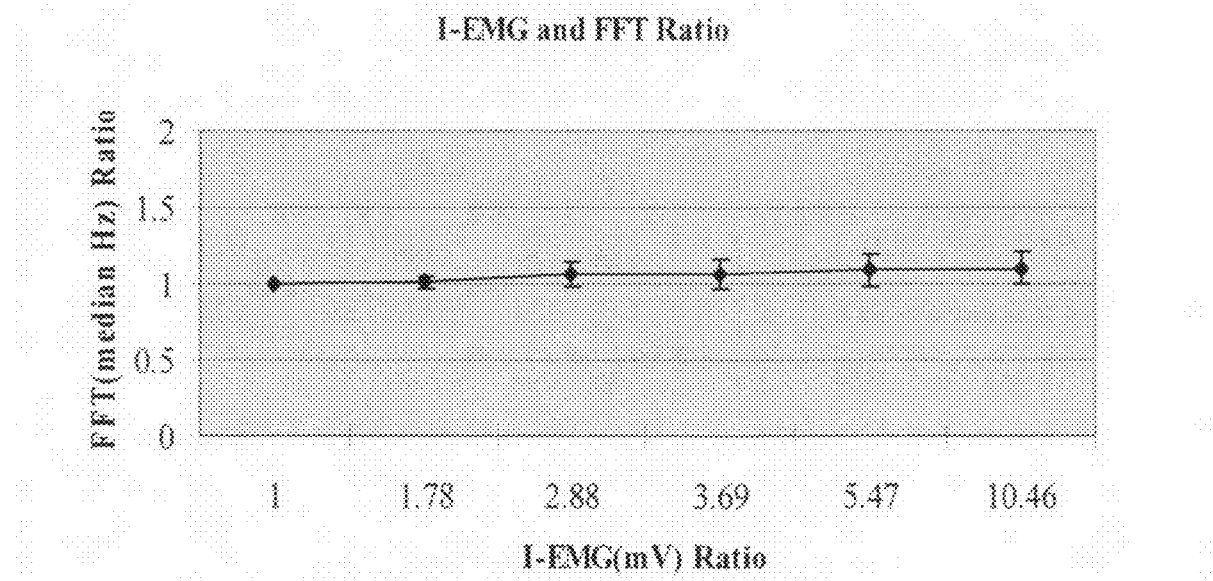
FIG. 6 illustrates the relationship between the FTT ratio and the I-EMG ratio. The Spearman's correlation coefficient was $R=0.466$, $p<0.01$, $N=14$. This demonstrates that the FFT ratio is directly correlated to the I-EMG ratio between the agonist and antagonist muscles.

As shown in FIG. 6, FFT (median Hz) was plotted as a function of I-EMG (mV)

The FFT increased with increasing I-EMG. This indicates that FTT and I-EMG are related to each other and the muscle hardness (tissue compliance).

EXAMPLE 2

Joint Study

In this example, neuromuscular electrical stimulation having a triphasic pulse train pattern was applied to the knee joint over a 24-week period to five patients. All of the patients exhibited evidence of osteoarthritis (radiographic and/or by patient symptoms report) in more than one joint; however, osteoarthritis of one knee has been the patient's primary complaint and the focus of treatment. The patients also exhibited a Kellgren and Lawrence osteoarthritis classification grade 1, 2 or 3 (i.e., indicative of cartilage still remaining in joint). The patients had also not undergone within 3 months of enrollment, corticosteroid or viscosupplementation (i.e., hyaluronate) injections to the effected knee. Further, the patient had not been on a stable dose for at least 3 months prior to enrollment of oral steroids, non-steroidal anti-inflammatories, or acetaminophen. If taking chondroprotective supplements (e.g., glucosamine and chondroitin sulfate), patient had not been on a stable dose for at least 3 months prior of enrollment. Table 1 summarizes the patient population:

TABLE 1

Patient Summary

| No. | Side | Age | KL(PF) | KL(FT) | Extension | Flexion |
|---|---|---|---|---|---|---|
| case 1 | Lt | 73 | 3 | 2 | −10 | 115 |
| case 2 | Lt | 73 | 3 | 2 | −20 | 135 |
| case 3 | Rt | 73 | 3 | 2 | −5 | 135 |
| case 4 | Lt | 62 | 2 | 2 | 0 | 140 |
| case 5 | Lt | 62 | 1 | 2 | −5 | 140 |

Patterned Neuromuscular Simulation for 20 min
3 times/week × 12 weeks

Figure 3P:
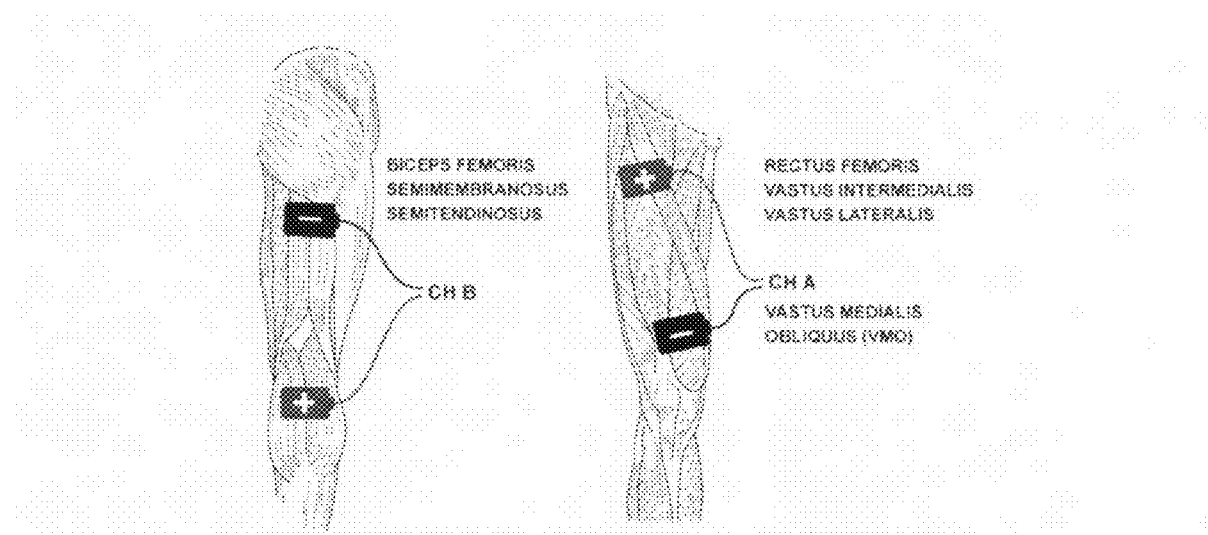
FIG. 3P illustrates a method for treating joint compression in a patient by applying electrical stimulation in accordance with a sixteenth exemplary embodiment of the present invention.

Each patient received a 20-minute session, to each affected knee, three times per week for 12 weeks. The neuromuscular electrical stimulation comprised a tri-phasic lower extremity stimulation pattern based on activation timing of the quadriceps and hamstrings for strength training. More specifically, the patient received 50 Hz impulses for 200 ms every 1500 ms) to establish a minimal twitch for 5 minutes and a moderate to strong, but well-tolerated twitch contractions for 15 minutes. The overlap period was 40 ills. The electrodes were placed on the patient as generally shown in FIG. 3P. The first pair of electrodes are positioned on the patient's skin on the vastus medialis and upper quadricep, and the second pair is positioned on the hamstring and triceps Surae muscles. Even though the exact mechanism of action for potential improvement of knee osteoarthritis and joint compression is not fully understood, it is hypothesized that when stimulating the muscles in this region that there may be an effect on changing the circulation of the synovial fluid, an effect on reducing disuse atrophy of the quadriceps and hamstrings, and an improvement in motor timing. The maximum peak output of the device is 10 mA into a 500 ohm load. The average current is very low because the pulse duration is only 70 microseconds at a pulse rate of 50 Hz. The average current would be approximately 4.5 mA average current into a 500 ohm load. The typical outputs used in stimulation varied from approximately 30-70 mA peak current or 1-3 mA average current.

Figure 7A:
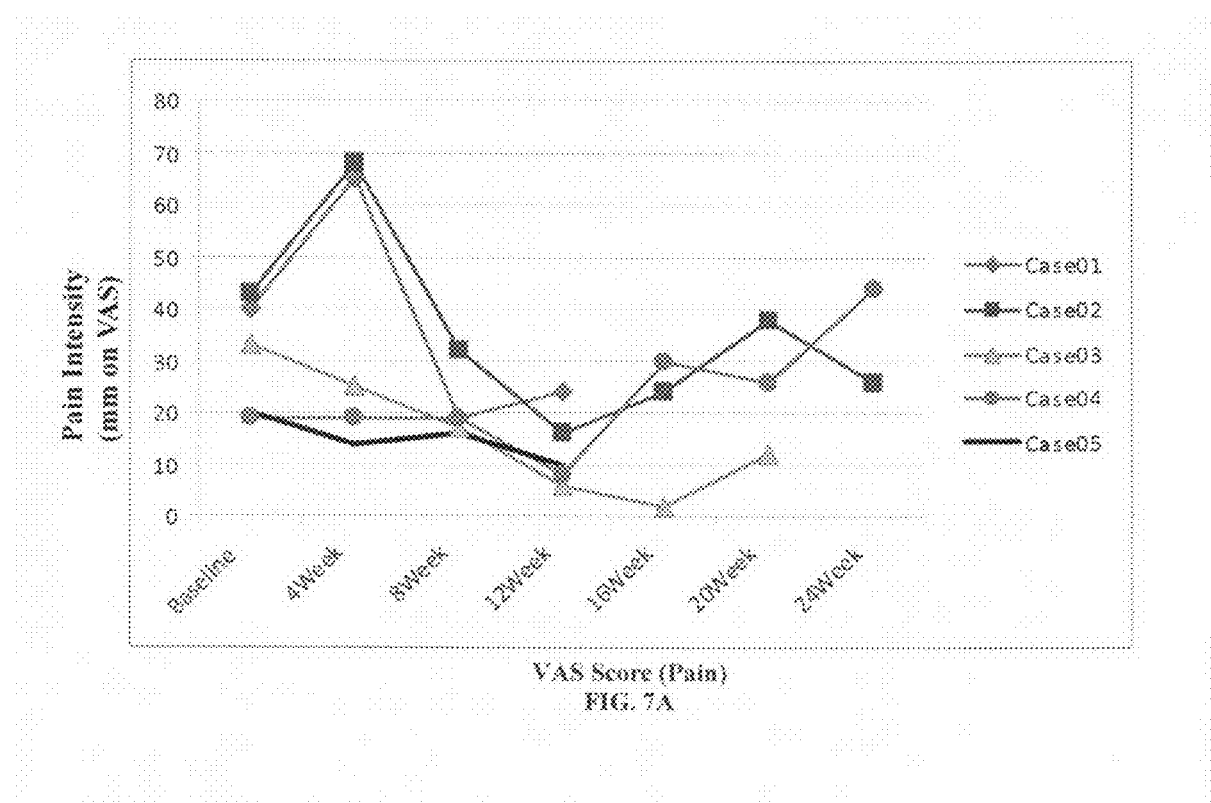
Figure 7B:
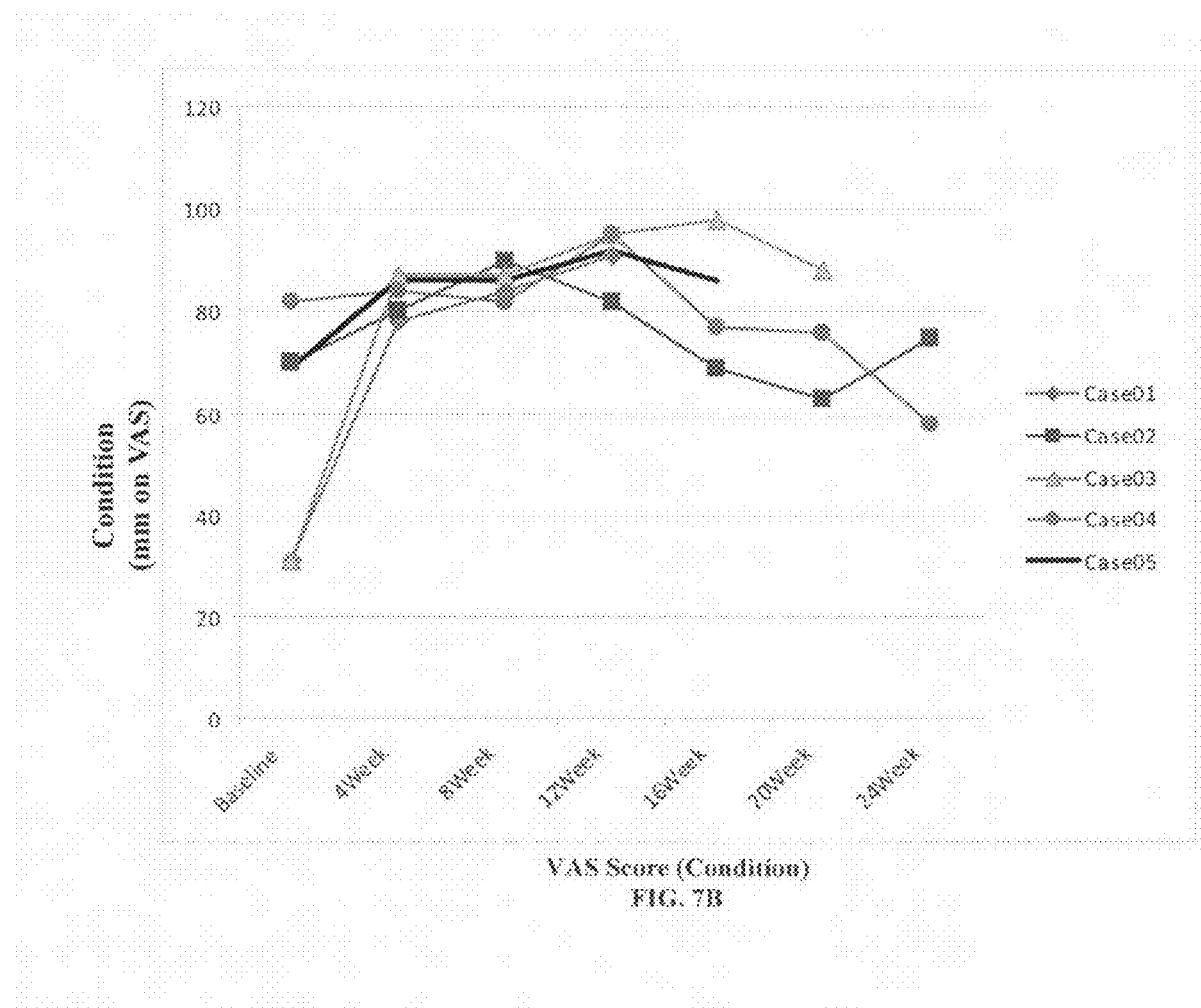
FIG. 7B illustrates the patients' reported overall condition
Figure 8:
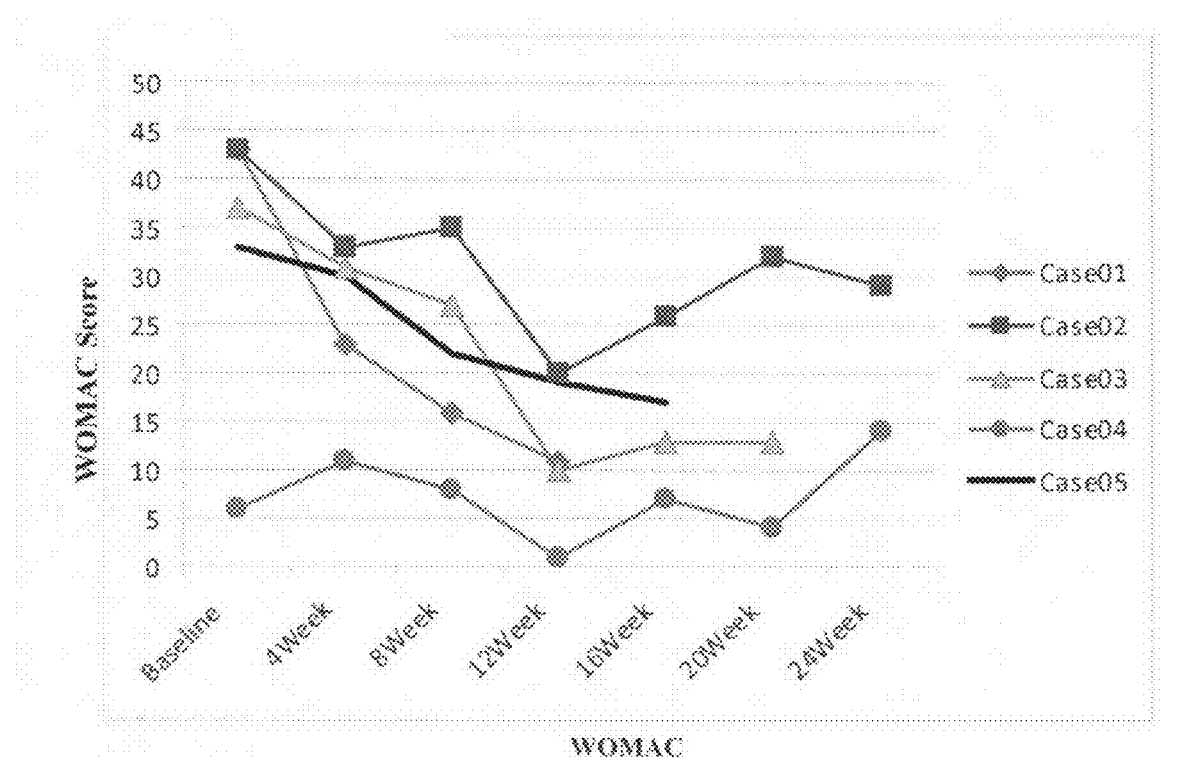
FIG. 8 illustrates the results of the Western Ontario Mac-Master 3.1 (WOMAC) tests performed on the five patients from Example 2.

FIG. 7A shows the Visual Analog Scores of the five patients over the treatment period on a 0 to 100 mm scale. In general, the patients' pain level increased (FIG. 7A), while their overall condition improved (FIG. 7B). The scale was be anchored at one end with "0" and labeled "no pain at all," and at the other "10" and labeled "worst pain possible." FIG. 8 illustrates the results of the Western Ontario MacMaster 3.1 (WOMAC), a 24-item validated test designed specifically for the assessment of lower extremity pain, stiffness, and physical function disability in osteoarthritis of the knee. WOMAC scores were very much higher (abnormal) prior to undergoing treatment.

Figure 9:
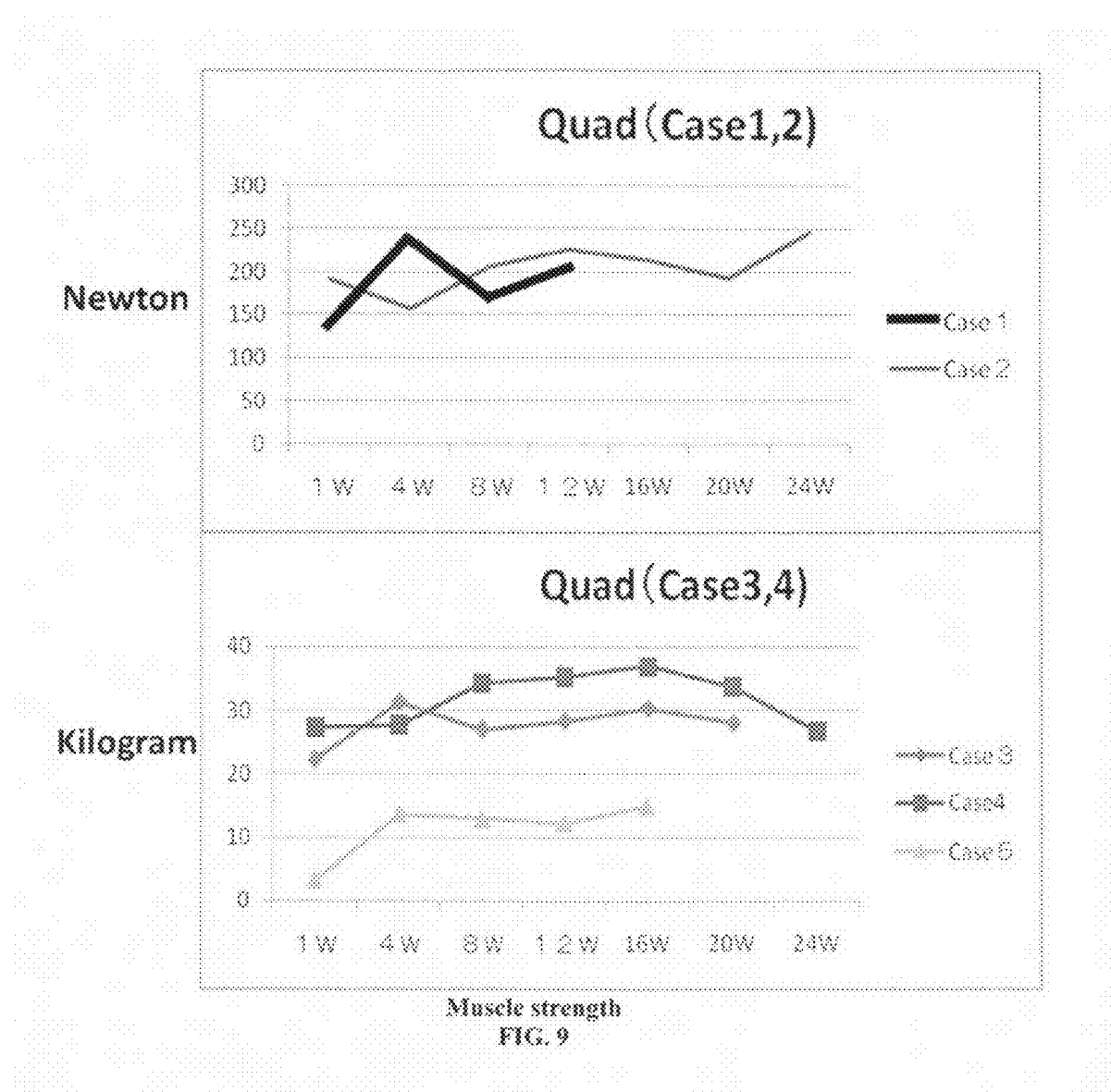
FIGS. 9 and 10 show the muscle strength of each patient throughout the course of treatment for the quadriceps, and hamstrings respectively for the five patients in Example 2.
Figure 10:
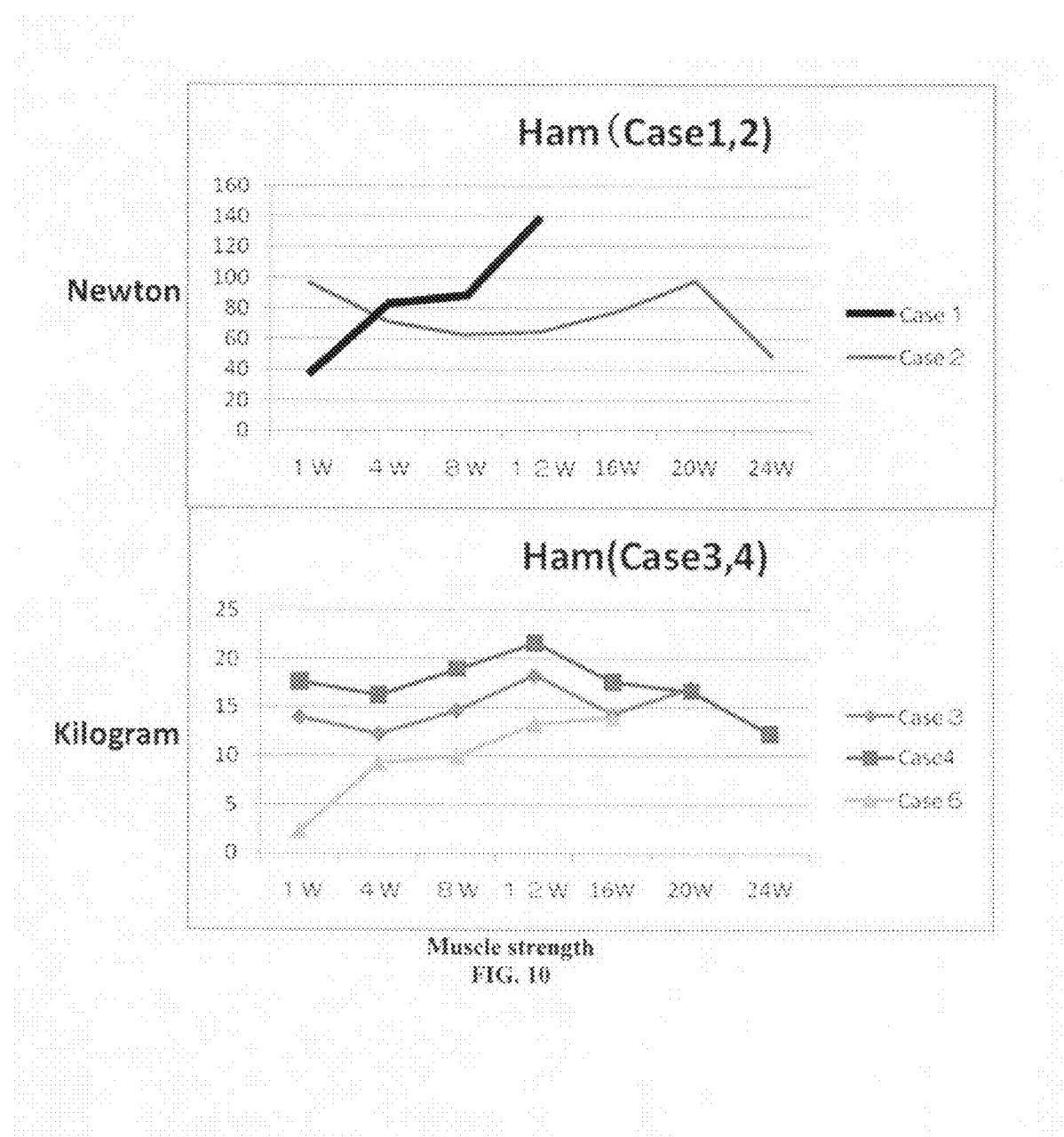

FIGS. 9 and 10 show the muscle strength of each patient throughout the course of treatment for the quadriceps, and hamstrings respectively. The strength of patients 1 and 2 was measured in Newtons, while that of patients 3, 4, and 5 was measured in kilograms. In general, the muscle strength improved over the course of treatment. The muscle strength was measured using a mechanical dynamometer.

Figure 11A:
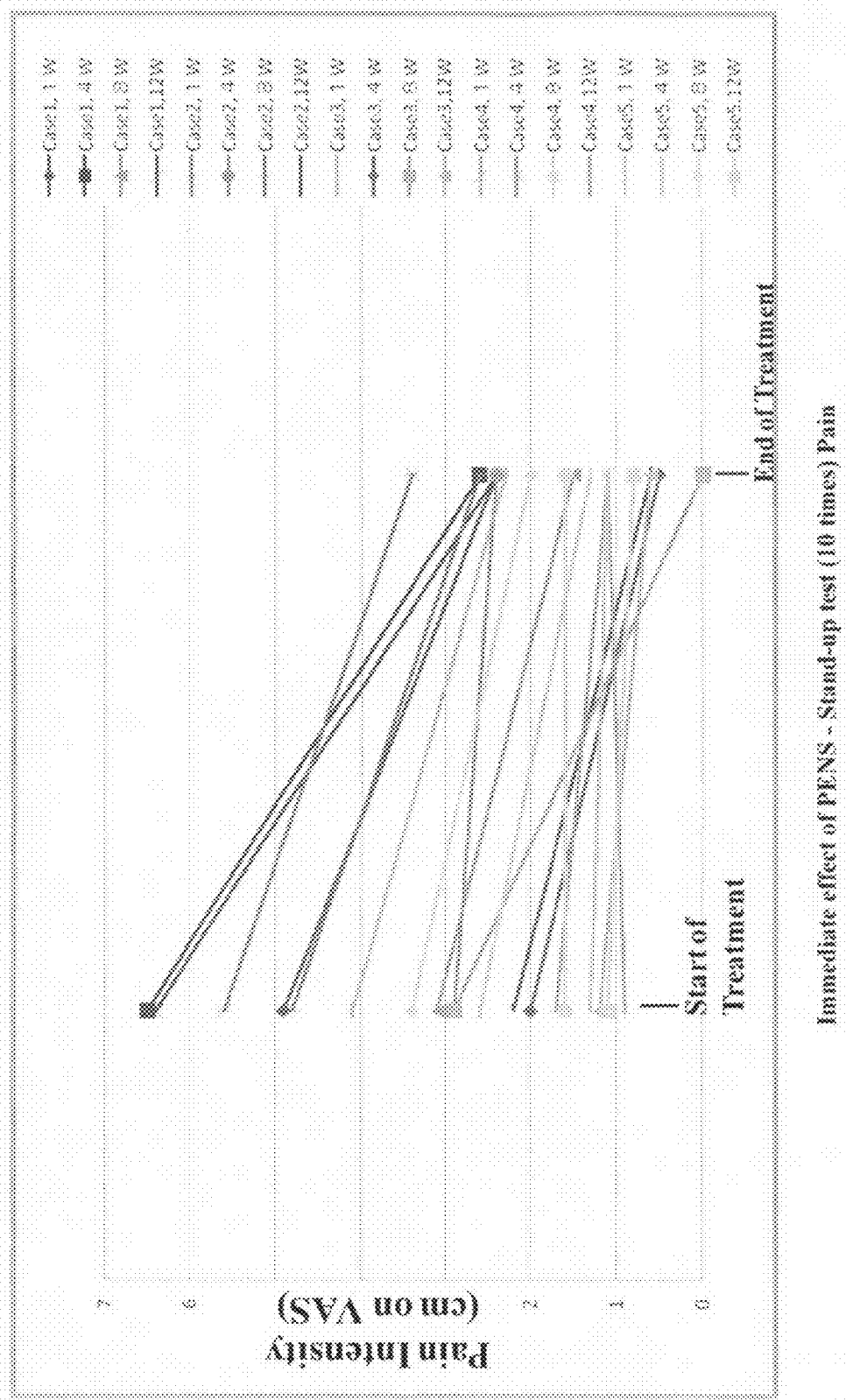
In FIG. 11A, the immediate effect of the patterned neuromuscular electrical stimulation is shown by the patients; VAS pain level.
Figure 11B:
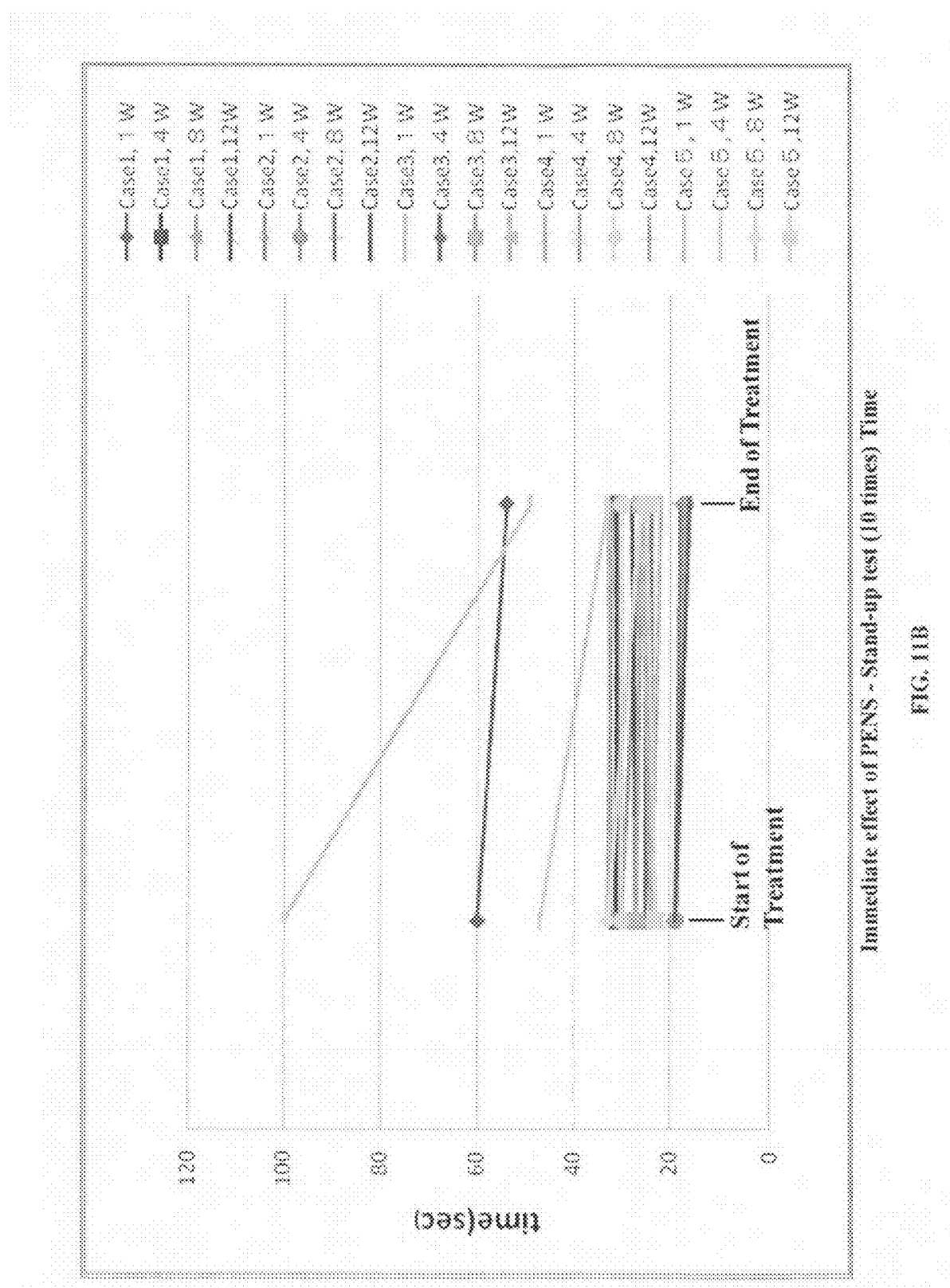
FIG. 11B illustrates the amount of time it took to complete the test for each patient.
Figure 11C:
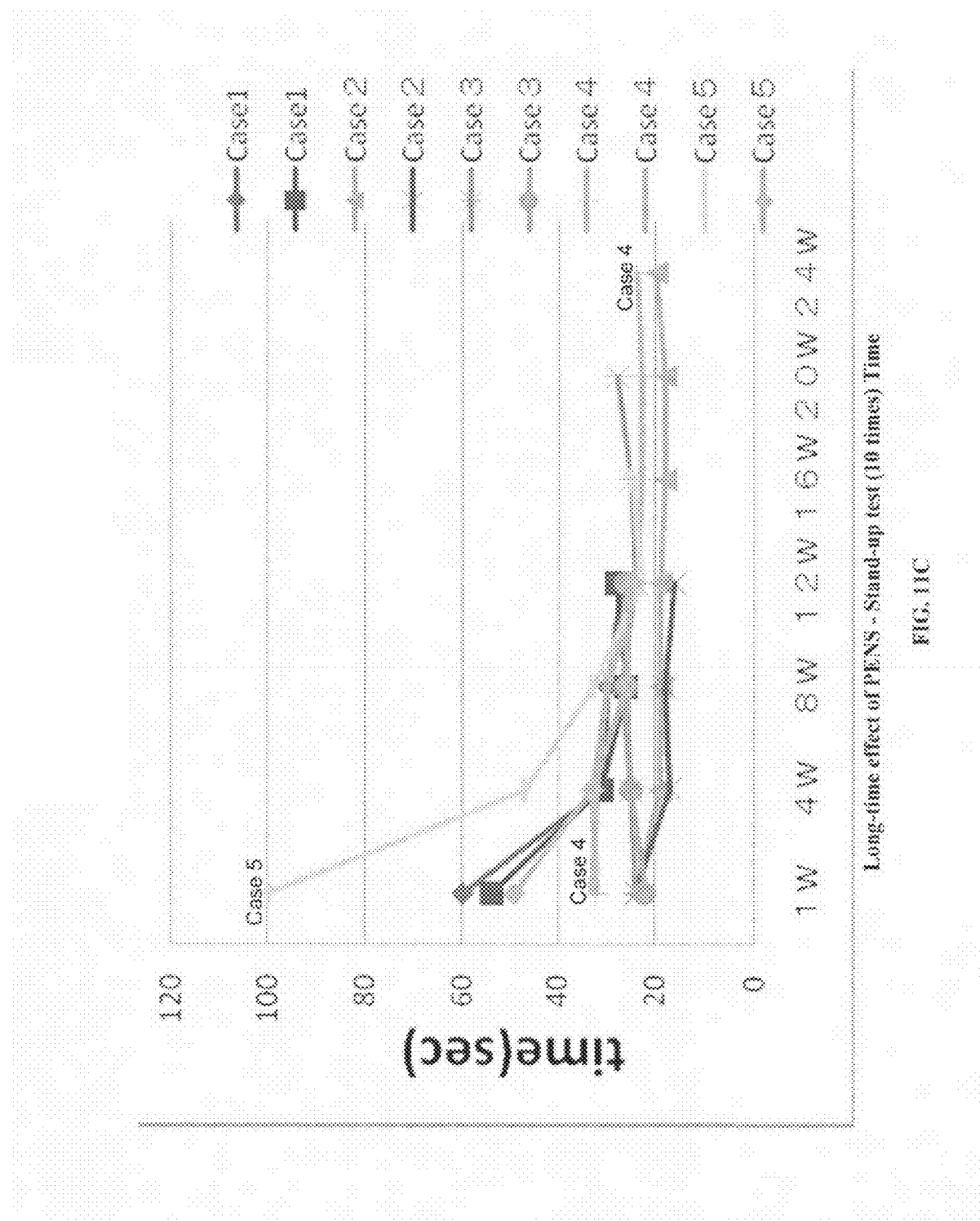
In FIG. 11C, the amount of time it took to complete the test was reported over the entire 24-week treatment course.

The immediate effect of a 20-minute treatment was also evaluated using a physical performance test. Patients were asked to stand up 10 times as fast as possible. FIG. 11A that the patient's VAS pain level decreased after most treatment sessions. Further, as shown in FIG. 11B, the amount of time it took to complete the test either decreased or was not changed as a result of the treatment session. As shown in FIG. 11C, over the entire 24-week treatment course, the amount of time it took it took to complete the test generally decreased.

The amount of fluid in the affected knee of each patient was also measured in order to assess the degree of inflammation in the joint. As shown in Table 2, in four of the five patients, the amount of fluid in the joint decreased by amount 2 ml. Thus, this indicates that the neuromuscular electrical stimulation was effective in decreasing inflammation.

TABLE 2

Joint Fluid

| No. | Joint Fluid Pre ml | Joint Fluid Post 12 weeks of treatment |
|---|---|---|
| Case 1 | 2 | 0 |
| Case 2 | 12 | 10 |
| Case 3 | 0 | N/A |
| Case 4 | 2 | 0 |
| Case 5 | 7 | 10 |

Lastly, delayed gadolinium-enhanced magnetic resonance imaging ("MRI") of cartilage ("dGEMRIC") was used in order to is used to examine the distribution of glycosaminoglycan in cartilage as generally described in Williams et al., *Delayed gadolinium-enhanced magnetic resonance imaging of cartilage in knee osteoarthritis: findings at different radiographic stages of disease and relationship to malalignment*, Arthritis Rheum. 2005 November; 52(11):3528-35, which is incorporated by reference. Glycosaminoglycans provide cartilage its compressive strength and the dGEMRIC technique uses a negatively charged MR contrast agent to determine the GAG distribution within the cartilage. Table 3 below shows that the relative intensity of the tibia and femur generally decreased. A negative pre-post reading indicates increased markers for cartilage.

TABLE 3

Relative intensity

| | Tibia | | | Femur | | |
|---|---|---|---|---|---|---|
| | Pre | Post | | Pre | Post | |
| Case 1 | 67.2 | 62.2 | −7.44% | 76.4 | 72.8 | −4.71% |
| Case 2 | 60.7 | 64.5 | 6.26% | 73.4 | 72.5 | −1.22% |
| Case 3 | 80.9 | 73.5 | −9.15% | 73.3 | 84.2 | 14.9% |
| Case 4 | 72.3 | 56.1 | −22.4% | 85.8 | 86.8 | 1.17% |
| Case 5 | 109 | 100 | −8.26% | 88.4 | 98 | 10.9% |

Together, these experiments indicate that joint compression decreased after applying the patterned neuromuscular electrical stimulation to the affected joint.

While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

What is claimed and desired to be secured by Letters Patent is as follows:

1. A method for reducing joint compression caused by co-contraction of antagonist and agonist muscles in a patient in need thereof comprising:
   applying neuromuscular electrical stimulation having a biphasic or triphasic pulse train pattern to at least two muscles associated with a target joint in said patient; and
   wherein said step of applying neuromuscular stimulation decreases co-contraction of said at least two muscles after said applying step;
   wherein said decreased co-contraction is measured by a decrease in pain at said target joint, improved muscle strength, decreased inflammation of said target joint, and an improved delayed gadolinium-enhanced magnetic resonance imaging of cartilage ("dGEMRIC") score.

2. The method of claim 1, wherein said step of applying neuromuscular electrical stimulation having a biphasic or triphasic pulse train pattern comprises:
   providing a first channel comprising two electrodes, wherein a first electrode of said first channel is positioned in electrical contact with tissue of a first muscle of said target joint of said patient and a second electrode of said first channel is positioned in electrical contact with tissue of said first muscle or a second muscle of said target joint of said patient;
   providing a second channel comprising two electrodes, wherein a first electrode of said second channel is positioned in electrical contact with tissue of said second muscle or a third muscle of said target joint of said patient and a second electrode of said second channel is positioned in electrical contact with tissue of said second muscle, third muscle or a fourth muscle of said target joint of said patient; and
   applying a series of electrical pulses having said biphasic or triphasic pulse train pattern to said target joint of said patient through said first and second channels in accordance with said procedure for reducing said joint compression.

3. The method of claim 2, wherein said first electrode of said first channel is positioned so as to stimulate a trapezius muscle of said patient, and said second electrode of said first channel is positioned so as to stimulate a cervical paraspinal muscle of said patient; and
   wherein said first and second electrodes of said second channel are positioned bilaterally so as to stimulate a second trapezius muscle and a second cervical paraspinal muscle of said patient.

4. The method of claim 2, wherein said first electrode of said first channel is positioned so as to stimulate a lower cervical paraspinal muscle and an upper thoracic paraspinal muscle of said patient, and said second electrode of said first channel is positioned so as to stimulate a cervical paraspinal muscle of said patient; and
   wherein said first and second electrodes of said second channel are positioned bilaterally so as to stimulate a second lower cervical paraspinal muscle, a second upper thoracic paraspinal muscle, and a second cervical paraspinal muscle of said patient.

5. The method of claim 2, wherein said first electrode of said first channel is positioned so as to stimulate a thoracic paraspinal muscle of said patient, and said second electrode of said first channel is positioned so as to stimulate an upper thoracic paraspinal muscle of said patient; and
   wherein said first and second electrodes of said second channel are positioned bilaterally so as to stimulate a second thoracic paraspinal muscle and a second upper thoracic paraspinal muscle of said patient.

6. The method of claim 2, wherein said first electrode of said first channel is positioned so as to stimulate a thoracic and/or lumbar paraspinal muscle of said patient, and said second electrode of said first channel is positioned so as to stimulate an abdominal muscle of said patient; and
   wherein said first and second electrodes of said second channel are positioned bilaterally so as to stimulate a second thoracic and/or lumbar paraspinal muscle and a second abdominal muscle of said patient.

7. The method of claim 2, wherein said first and second channels each further comprise a third electrode and a fourth electrode;
   wherein said first and second electrodes of said first channel are positioned so as to stimulate a multifidus muscle of said patient, and said third and fourth electrodes of said first channel are positioned so as to stimulate an abdominal muscle of said patient; and
   wherein said first, second, third, and fourth electrodes of said second channel are positioned bilaterally so as to stimulate a second multifidus muscle and a second abdominal muscle of said patient.

8. The method of claim 2, wherein said first and second electrodes of said first channel are positioned so as to stimulate a biceps brachii muscle of said patient; and
   wherein said first and second electrodes of said second channel are positioned so as to stimulate a triceps brachii muscle of said patient.

9. The method of claim 2, wherein said first electrode of said first channel is positioned so as to stimulate a biceps brachii muscle of said patient, and said second electrode of said first channel is positioned so as to stimulate a pectoralis major muscle and an anterior deltoid muscle of said patient; and
   wherein said first electrode of said second channel is positioned so as to stimulate a triceps brachii muscle of said patient, and said second electrode of said second channel is positioned so as to stimulate an infraspinatus teres minor muscle and a posterior deltoid muscle of said patient.

10. The method of claim 2, wherein said first electrode of said first channel is positioned so as to stimulate a biceps brachii muscle of said patient, and said second electrode of said first channel is positioned so as to stimulate an anterior deltoid muscle of said patient; and
wherein said first electrode of said second channel is positioned so as to stimulate a triceps brachii muscle of said patient, and said second electrode of said second channel is positioned so as to stimulate a posterior deltoid muscle of said patient.

11. The method of claim 2, wherein said first electrode of said first channel is positioned so as to stimulate a flexor muscle of a hand of said patient selected from a group consisting of flexor digitorum superficialis and flexor digitorum profundus, and said second electrode of said first channel is positioned so as to stimulate a flexor muscle of a wrist of said patient selected from the group consisting of flexor carpi ulnaris and flexor carpi radialis; and
wherein said first electrode of said second channel is positioned so as to stimulate an extensor muscle of said hand of said patient selected from the group consisting of extensor digitorum and extensor digiti minimi, and said second electrode of said second channel is positioned so as to stimulate an extensor muscle of said wrist of said patient selected from the group consisting of extensor carpi ulnaris and extensor carpi radialis.

12. The method of claim 2, wherein said first electrode of said first channel is positioned so as to stimulate a flexor muscle of a hand of said patient, and said second electrode of said first channel is positioned so as to stimulate a biceps brachii muscle of said patient; and
wherein said first electrode of said second channel is positioned so as to stimulate an extensor forearm muscle of said patient, and said second electrode of said second channel is positioned so as to stimulate a triceps brachii muscle of said patient.

13. The method of claim 2, wherein said first electrode of said first channel is positioned so as to stimulate an extensor digitorum brevis muscle of said patient, and said second electrode of said first channel is positioned so as to stimulate a tibialis anterior muscle, an extensor digitorum longus muscle, and/or an extensor hallucis longus muscle of said patient; and
wherein said first electrode of said second channel is positioned so as to stimulate an intrinsic foot muscle of said patient, and said second electrode of said second channel is positioned so as to stimulate a posterior tibialis muscle and a flexor hallucis muscle of said patient.

14. The method of claim 2, wherein said first and second electrodes of said first channel are positioned so as to stimulate a tibialis anterior muscle and an optional peroneus muscle of said patient; and
wherein said first and second electrodes of said second channel are positioned so as to stimulate a triceps surae of said patient.

15. The method of claim 2, wherein said first electrode of said first channel is positioned so as to stimulate a tibialis anterior muscle of said patient, and said second electrode of said first channel is positioned so as to stimulate a quadriceps muscle of a leg of said patient; and
wherein said first electrode of said second channel is positioned so as to stimulate a triceps surae of said patient, and said second electrode of said second channel is positioned so as to stimulate a hamstring muscle of said leg of said patient.

16. The method of claim 2, wherein said first electrode of said first channel is positioned so as to stimulate a vastus medialis muscle of said patient, and said second electrode of said first channel is positioned so as to stimulate a gluteus medius muscle, a gluteus minimus muscle, and a tensor fasciae latae muscle of said patient; and
wherein said first electrode of said second channel is positioned so as to stimulate a biceps femoris muscle, a semitendinosus muscle, and/or a semimembraneous muscle of said patient, and said second electrode of said second channel is positioned so as to stimulate an adductor magnus muscle, an adductor longus muscle, an adductor brevis muscle, and a medial hamstring muscle of said patient.

17. The method of claim 2, wherein said first electrode of said first channel is positioned so as to stimulate a rectus femoris muscle and/or a vastus lateralis muscle of said patient, and said second electrode of said first channel is positioned so as to stimulate a vastus medialis muscle of said patient; and
wherein said first and second electrodes of said second channel are positioned so as to stimulate a biceps femoris muscle, a semimembranosus muscle, and/or a semitendinosus muscle of said leg of said patient.

18. The method of claim 2, wherein said series of electrical pulses comprises a plurality of cycles of a biphasic sequential pulse train pattern; and
wherein said biphasic sequential pulse train pattern comprises a first phase of electrical pulses applied to said first channel and a second phase of electrical pulses applied to said second channel, and wherein said second phase of electrical pulses commences after termination of said first phase of electrical pulses.

19. The method of claim 2, wherein said series of electrical pulses comprises a plurality of cycles of a biphasic overlapping pulse train pattern; and
wherein said biphasic overlapping pulse train pattern comprises a first phase of electrical pulses applied to said first channel and a second phase of electrical pulses applied to said second channel, and wherein said second phase of electrical pulses commences before termination of said first phase of electrical pulses.

20. The method of claim 2, wherein said series of electrical pulses comprises a plurality of cycles of a triphasic sequential pulse train pattern;
wherein said triphasic sequential pulse train pattern comprises a first phase of electrical pulses applied to said first channel, a second phase of electrical pulses applied to said second channel, and a third phase of electrical pulses applied to said first channel; and
wherein said second phase of electrical pulses commences after termination of said first phase of electrical pulses and said third phase of electrical pulses commences after termination of said second phase of electrical pulses.

21. The method of claim 2, wherein said series of electrical pulses comprises a plurality of cycles of a triphasic overlapping pulse train pattern;
wherein said triphasic overlapping pulse train pattern comprises a first phase of electrical pulses applied to said first channel, a second phase of electrical pulses applied to said second channel, and a third phase of electrical pulses applied to said first channel; and
wherein said second phase of electrical pulses commences before termination of said first phase of electrical pulses and said third phase of electrical pulses commences before termination of said second phase of electrical pulses.

22. The method of claim 2, wherein said first electrode of said first channel is positioned so as to stimulate an upper quadricep muscle of said patient, and said second electrode of said first channel is positioned so as to stimulate a vastus medialis muscle of said patient; and
   wherein said first electrode of said second channel is positioned so as to stimulate a hamstring muscle of said patient, and said second electrode of said second channel is positioned so as to stimulate a triceps surae muscle of said patient.

23. The method of claim 1, wherein said decreased co-contraction is also determined using EMG.

24. The method of claim 1, wherein said decreased co-contraction is also determined using a tissue hardness and tissue compliance measuring system.

25. The method of claim 1, further comprising a step of co-administering said electrical stimulation to said patient and a therapeutically effective amount of an agent selected from a group consisting of nonsteroidal anti-inflammatory drugs (NSAIDS) or analgesics; tramadol; codeine; propoxyphene; glucosamine; chondroitin sulfate; salicylates; Cox-2 NSAIDS; surface application of capsaicin cream 0.25%; steroids, corticosteroids, or hyaluronic acid preparations.

26. The method of claim 1, wherein a delay between each said pulse train pattern is between 400 milliseconds and 1200 milliseconds.

27. The method of claim 1 wherein said decreased co-contraction is also measured by a decrease in the I-EMG in said at least two target muscles of said patient at rest or at a predetermined load.

28. The method of claim 1 wherein said decreased co-contraction is also measured by a decrease in the FFT in said at least two target muscles of said patient at rest or at a predetermined load.

29. The method of claim 1 wherein said decreased co-contraction is also measured by a decrease in the hardness of said at least two target muscles using a tissue hardness and tissue compliance measurement system.

* * * * *